(12) United States Patent
Tanuma et al.

(10) Patent No.: US 7,402,310 B2
(45) Date of Patent: Jul. 22, 2008

(54) DEOXYRIBONUCLEASE, GENE ENCODING SAME AND USE THEREOF

(75) Inventors: Sei-ichi Tanuma, 3-13-11, Chuo, Ota-ku, Tokyo (JP) 143-0024; Daisuke Shiokawa, Tokyo (JP)

(73) Assignee: Sei-ichi Tanuma, Hachioji-shi (JP)

( * ) Notice: Subject to any disclaimer, the term of this patent is extended or adjusted under 35 U.S.C. 154(b) by 0 days.

(21) Appl. No.: 11/335,754

(22) Filed: Jan. 19, 2006

(65) Prior Publication Data

US 2006/0110770 A1   May 25, 2006

Related U.S. Application Data

(62) Division of application No. 10/670,863, filed on Sep. 25, 2003, now Pat. No. 7,049,123, which is a division of application No. 09/807,784, filed on Jul. 3, 2001, now Pat. No. 6,653,118.

(51) Int. Cl.
*A61K 38/46* (2006.01)
*C07K 14/00* (2006.01)
*C12N 9/16* (2006.01)
*C12Q 1/44* (2006.01)
C07H 21/00 (2006.01)
C12N 15/00 (2006.01)
C12N 1/21 (2006.01)
C12N 5/10 (2006.01)
C12P 21/00 (2006.01)

(52) U.S. Cl. .................. 424/94.6; 435/196; 435/19; 435/320.1; 435/69.1; 435/252.3; 435/325; 530/350; 536/23.2

(58) Field of Classification Search .................. 435/196, 435/19, 94.6, 320.1, 69.1, 252.3, 325; 530/350; 536/23.2, 23.5

See application file for complete search history.

(56) References Cited

U.S. PATENT DOCUMENTS 5,821,103 A   10/1998   Tanuma 6,358,723 B1   3/2002   Eastman et al.

FOREIGN PATENT DOCUMENTS

| EP | 0 853 121 A2 | 8/1998 |
|---|---|---|
| EP | 0 853 121 A3 | 8/1998 |
| WO | WO 97/28266 A1 | 8/1997 |
| WO | WO 97/40134 A3 | 10/1997 |

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Bernardi, *The Enzymes* (3rd Ed., Boyer, P.D., ed.) 4, Chapter 11: 271-287, Academic Press, New York (1971).
Zeng et al., *Biochemical and Biophysical Research Communications*, 231(2): 499-504 (1997).
Shiokawa et al., *Nucl. Acids Res.*, 27(20): 4083-4089 (Oct. 1999).
Tanuma et al., *Biochemical and Biophysical Research Communications*, 265(2): 395-399 (Nov. 1999).
Weekes et al., Dornase Alfa: A Position Statement of the NSW Therapeutic Assessment Group Inc., pp. 1-12 (1995).
Zahm et al., *Am. J. Respir. Crit. Care Med*, 163: 1153-1157 (2001).

* cited by examiner

*Primary Examiner*—Delia M Ramirez
(74) *Attorney, Agent, or Firm*—Leydig, Voit & Mayer, Ltd.

(57) ABSTRACT

This invention provides a novel acid DNase (DLAD) which is an endonuclease capable of cleaving DNA independently from divalent cations, under acidic conditions, which retains its activity in acidic to even neutral pH range, and which is not inhibited by G-actin. This invention also provides a DNA encoding the enzyme, an expression vector containing the DNA, and a host cell transformed with the expression vector. Furthermore, a pharmaceutical composition containing DLAD, DLAD expression vector or a host cell transformed with the expression vector as an active ingredient is provided. The pharmaceutical composition is useful as a therapeutic agent replacing DNase I for cystic fibrosis, and can provide a new approach for the prophylaxis and treatment of infectious diseases.

3 Claims, 3 Drawing Sheets

Concentration

SEQUENCE LISTING

<160> NUMBER OF SEQ ID NOS: 15

<210> SEQ ID NO 1
<211> LENGTH: 354
<212> TYPE: PRT
<213> ORGANISM: Mus musculus

<400> SEQUENCE: 1

```
Met Thr Ala Lys Pro Leu Arg Thr Val Leu Ser Leu Leu Phe Phe Ala
            -20              -15             -10

Leu Ser Gly Val Leu Gly Thr Pro Glu Ile Ser Cys Arg Asn Glu Tyr
    -5                    1               5                  10

Gly Glu Ala Val Asp Trp Phe Ile Phe Tyr Lys Leu Pro Lys Arg Thr
                15                  20              25

Ser Lys Ala Ser Glu Glu Ala Gly Leu Gln Tyr Leu Tyr Leu Asp Ser
                30                  35              40

Thr Arg Gln Thr Trp Asn Lys Ser Leu Tyr Leu Ile Asn Ser Thr Arg
            45                  50              55

Ser Ala Leu Gly Arg Thr Leu Gln His Leu Tyr Asp Thr His Asn Ser
        60                  65              70

Thr Asn Asp Thr Ala Tyr Leu Ile Tyr Asn Asp Gly Val Pro Gly Ser
75                  80                  85                  90

Val Asn Tyr Ser Arg Gln Tyr Gly His Ala Lys Gly Leu Leu Val Trp
                95                  100             105

Asn Arg Thr Gln Gly Phe Trp Leu Ile His Ser Val Pro Lys Phe Pro
            110                 115             120

Pro Val His Gly Tyr Glu Tyr Pro Thr Ser Gly Arg Arg Tyr Gly Gln
            125                 130             135

Thr Gly Ile Cys Ile Thr Phe Gly Tyr Ser Gln Phe Glu Glu Ile Asp
        140                 145             150

Phe Gln Leu Leu Val Leu Gln Pro Asn Ile Tyr Ser Cys Phe Ile Pro
155                 160                 165                 170

Ser Thr Phe His Trp Lys Leu Ile Tyr Met Pro Arg Met Cys Ala Asn
                175                 180             185

Ser Ser Ser Leu Lys Ile Pro Val Arg Tyr Leu Ala Glu Leu His Ser
            190                 195             200

Ala Gln Gly Leu Asn Phe Val His Phe Ala Lys Ser Ser Phe Tyr Thr
            205                 210             215

Asp Asp Ile Phe Thr Gly Trp Ile Ala Gln Lys Leu Lys Thr His Leu
        220                 225             230

Leu Ala Gln Thr Trp Gln Lys Lys Gln Glu Leu Pro Ser Asn Cys
235                 240                 245                 250

Ser Leu Pro Tyr His Val Tyr Asn Ile Lys Ser Ile Gly Val Thr Ser
                255                 260             265

Lys Ser Tyr Phe Ser Ser Arg Gln Asp His Ser Lys Trp Cys Val Ser
            270                 275             280

Ile Lys Gly Ser Ala Asn Arg Trp Thr Cys Ile Gly Asp Leu Asn Arg
        285                 290             295

Ser Leu His Gln Ala Leu Arg Gly Gly Phe Ile Cys Thr Lys Asn
        300                 305             310

His Tyr Ile Tyr Gln Ala Phe His Lys Leu Tyr Leu Arg Tyr Gly Phe
315                 320                 325                 330

Cys Lys
```

```
<210> SEQ ID NO 2
<211> LENGTH: 1652
<212> TYPE: DNA
<213> ORGANISM: Mus Musculus
<220> FEATURE:
<221> NAME/KEY: CDS
<222> LOCATION: (213)..(1274)

<400> SEQUENCE: 2
ctagtcgaca actgagcaca aaggctccca gagtcacact ggaatgttgt gacagaaccc      60
atcagatgac atgggactca gcctcttctg tttgtgccca acagtgaac agcaaaagtg     120 aaccgacccg caagggagcc aacgcggcct gagaaagacc tgacactctg actccacagt    180
cccctgcatg gaatgaaggc cacagataga aa atg aca gca aag cct cta aga      233
                                   Met Thr Ala Lys Pro Leu Arg
                                              -20 aca gtt ctt tct ttg ctc ttc ttt gcc ctc tct ggg gtc ctg ggg aca      281
Thr Val Leu Ser Leu Leu Phe Phe Ala Leu Ser Gly Val Leu Gly Thr
-15                 -10                 -5                    1 cca gaa atc tca tgc aga aat gaa tat ggt gaa gct gtg gac tgg ttt      329
Pro Glu Ile Ser Cys Arg Asn Glu Tyr Gly Glu Ala Val Asp Trp Phe
            5                   10                  15 atc ttt tat aag tta ccc aaa agg act agc aag gca agt gaa gag gcg      377
Ile Phe Tyr Lys Leu Pro Lys Arg Thr Ser Lys Ala Ser Glu Glu Ala
        20                  25                  30 ggg ctg cag tac ctg tac ctg gac tcc aca aga caa acc tgg aac aag      425
Gly Leu Gln Tyr Leu Tyr Leu Asp Ser Thr Arg Gln Thr Trp Asn Lys
    35                  40                  45 agc ctc tac ctg att aac agc acc agg agt gct ctg ggg agg acc tta      473
Ser Leu Tyr Leu Ile Asn Ser Thr Arg Ser Ala Leu Gly Arg Thr Leu
50                  55                  60                  65 cag cat ctg tat gac aca cat aat tcc acg aat gac aca gcc tat cta      521
Gln His Leu Tyr Asp Thr His Asn Ser Thr Asn Asp Thr Ala Tyr Leu
                70                  75                  80 ata tac aac gat ggt gtc cct gga tct gtg aat tac agc aga cag tat      569
Ile Tyr Asn Asp Gly Val Pro Gly Ser Val Asn Tyr Ser Arg Gln Tyr
            85                  90                  95 gga cat gcc aaa ggt ctg ctg gta tgg aac aga acg cag ggg ttc tgg      617
Gly His Ala Lys Gly Leu Leu Val Trp Asn Arg Thr Gln Gly Phe Trp
        100                 105                 110 ctg ata cac tct gtt ccc aag ttt ccc cca gtt cat ggc tat gag tac      665
Leu Ile His Ser Val Pro Lys Phe Pro Pro Val His Gly Tyr Glu Tyr
    115                 120                 125 cca acc tcg ggg agg cga tat gga caa acc ggc atc tgc atc act ttc      713
Pro Thr Ser Gly Arg Arg Tyr Gly Gln Thr Gly Ile Cys Ile Thr Phe
130                 135                 140                 145 gga tac agc cag ttt gag gaa ata gat ttt cag ctc ttg gtc tta caa      761
Gly Tyr Ser Gln Phe Glu Glu Ile Asp Phe Gln Leu Leu Val Leu Gln
                150                 155                 160 cca aac atc tac agc tgc ttc att cca agc acc ttt cac tgg aaa ctt      809
Pro Asn Ile Tyr Ser Cys Phe Ile Pro Ser Thr Phe His Trp Lys Leu
            165                 170                 175 atc tac atg ccc cgg atg tgt gcc aac tcc agt cct tta aag atc cct      857
Ile Tyr Met Pro Arg Met Cys Ala Asn Ser Ser Pro Leu Lys Ile Pro
        180                 185                 190 gtc cgg tac ctc gct gaa ctg cac tca gcc cag ggt cta aac ttc gtc      905
Val Arg Tyr Leu Ala Glu Leu His Ser Ala Gln Gly Leu Asn Phe Val
    195                 200                 205 cat ttt gca aaa tca agt ttt tat act gat gac atc ttt aca gga tgg      953
His Phe Ala Lys Ser Ser Phe Tyr Thr Asp Asp Ile Phe Thr Gly Trp
```

-continued

```
His Phe Ala Lys Ser Ser Phe Tyr Thr Asp Asp Ile Phe Thr Gly Trp
210                 215                 220                 225 ata gct caa aag ttg aag aca cat ttg tta gca caa acc tgg cag aaa    1001
Ile Ala Gln Lys Leu Lys Thr His Leu Leu Ala Gln Thr Trp Gln Lys
                230                 235                 240 aag aaa caa gag ctt cct tca aac tgt tcc ctg cct tac cat gtc tac    1049
Lys Lys Gln Glu Leu Pro Ser Asn Cys Ser Leu Pro Tyr His Val Tyr
        245                 250                 255 aac atc aag tcc att ggg gta act tcc aag tct tac ttc agt tct cgc    1097
Asn Ile Lys Ser Ile Gly Val Thr Ser Lys Ser Tyr Phe Ser Ser Arg
    260                 265                 270 caa gac cat tcc aaa tgg tgt gtt tcc ata aag ggc tcc gca aat cgc    1145
Gln Asp His Ser Lys Trp Cys Val Ser Ile Lys Gly Ser Ala Asn Arg
275                 280                 285 tgg acc tgc att gga gac cta aat cga agc cta cac caa gcc tta aga    1193
Trp Thr Cys Ile Gly Asp Leu Asn Arg Ser Leu His Gln Ala Leu Arg
290                 295                 300                 305 ggt gga gga ttc atc tgt aca aag aat cac tac att tac cag gca ttt    1241
Gly Gly Gly Phe Ile Cys Thr Lys Asn His Tyr Ile Tyr Gln Ala Phe
                310                 315                 320 cat aaa tta tat ctc cgt tat ggg ttc tgt aag taaactcggt gaaaggccac   1294
His Lys Leu Tyr Leu Arg Tyr Gly Phe Cys Lys
        325                 330 accctctgtc cttgaaaaca ctggcactgg aacatctcgc cttggatctg ttctccataa   1354
tttcaaggct tctgagtgag cacaacgtag cgtccaataa aagcactgtg agcccacatt   1414
taccttccta tgttcaaatc aagagaaata ggagtcatct gcatgtatgg aattagaaat   1474
caaaatcatg atatgtaagt aatagcacca ggggacagaa tacaatattt tcctccagtt   1534
taattacctt cagtggtctg tcttgtggat taagtttcat ctctcacaaa gcaaccctga   1594
ctgtcctgtt tgaagaaata aaggtgccct cctccccctt aaaaaaaaaa aaaaaaaa     1652

<210> SEQ ID NO 3
<211> LENGTH: 361
<212> TYPE: PRT
<213> ORGANISM: Homo sapiens

<400> SEQUENCE: 3

Met Lys Gln Lys Met Met Ala Arg Leu Leu Arg Thr Ser Phe Ala Leu
        -25                 -20                 -15

Leu Phe Leu Gly Leu Phe Gly Val Leu Gly Ala Ala Thr Ile Ser Cys
-10                 -5                   1                   5

Arg Asn Glu Glu Gly Lys Ala Val Asp Trp Phe Thr Phe Tyr Lys Leu
                10                  15                  20

Pro Lys Arg Gln Asn Lys Glu Ser Gly Glu Thr Gly Leu Glu Tyr Leu
        25                  30                  35

Tyr Leu Asp Ser Thr Thr Arg Ser Trp Arg Lys Ser Glu Gln Leu Met
        40                  45                  50

Asn Asp Thr Lys Ser Val Leu Gly Arg Thr Leu Gln Gln Leu Tyr Glu
55                  60                  65

Ala Tyr Ala Ser Lys Ser Asn Asn Thr Ala Tyr Leu Ile Tyr Asn Asp
70                  75                  80                  85

Gly Val Pro Lys Pro Val Asn Tyr Ser Arg Lys Tyr Gly His Thr Lys
                90                  95                  100

Gly Leu Leu Leu Trp Asn Arg Val Gln Gly Phe Trp Leu Ile His Ser
        105                 110                 115
```

```
Ile Pro Gln Phe Pro Pro Ile Pro Glu Glu Gly Tyr Asp Tyr Pro Pro
        120                 125                 130

Thr Gly Arg Arg Asn Gly Gln Ser Gly Ile Cys Ile Thr Phe Lys Tyr
    135                 140                 145

Asn Gln Tyr Glu Ala Ile Asp Ser Gln Leu Leu Val Cys Asn Pro Asn
150                 155                 160                 165

Val Tyr Ser Cys Ser Ile Pro Ala Thr Phe His Gln Glu Leu Ile His
                170                 175                 180

Met Pro Gln Leu Cys Thr Arg Ala Ser Ser Glu Ile Pro Gly Arg
            185                 190                 195

Leu Leu Thr Thr Leu Gln Ser Ala Gln Gly Gln Lys Phe Leu His Phe
        200                 205                 210

Ala Lys Ser Asp Ser Phe Leu Asp Gly Ile Phe Ala Ala Trp Met Ala
    215                 220                 225

Gln Arg Leu Lys Thr His Leu Leu Thr Glu Thr Trp Gln Arg Lys Arg
230                 235                 240                 245

Gln Glu Leu Pro Ser Asn Cys Ser Leu Pro Tyr His Val Tyr Asn Ile
                250                 255                 260

Lys Ala Ile Lys Leu Ser Arg His Ser Tyr Phe Ser Ser Tyr Gln Asp
            265                 270                 275

His Ala Lys Trp Cys Ile Ser Gln Lys Gly Thr Lys Asn Arg Trp Thr
        280                 285                 290

Cys Ile Gly Asp Leu Asn Arg Ser Pro His Gln Ala Phe Arg Ser Gly
    295                 300                 305

Gly Phe Ile Cys Thr Gln Asn Trp Gln Ile Tyr Gln Ala Phe Gln Gly
310                 315                 320                 325

Leu Val Leu Tyr Tyr Glu Ser Cys Lys
                330

<210> SEQ ID NO 4
<211> LENGTH: 1086
<212> TYPE: DNA
<213> ORGANISM: Homo sapiens
<220> FEATURE:
<221> NAME/KEY: CDS
<222> LOCATION: (1)..(1083)

<400> SEQUENCE: 4 atg aaa cag aaa atg atg gca aga ctg cta aga aca tcc ttt gct ttg      48
Met Lys Gln Lys Met Met Ala Arg Leu Leu Arg Thr Ser Phe Ala Leu
        -25                 -20                 -15 ctc ttc ctt ggc ctc ttt ggg gtg ctg ggg gca gca aca att tca tgc      96
Leu Phe Leu Gly Leu Phe Gly Val Leu Gly Ala Ala Thr Ile Ser Cys
    -10                 -5                  1                   5 aga aat gaa gaa ggg aaa gct gtg gac tgg ttt act ttt tat aag tta     144
Arg Asn Glu Glu Gly Lys Ala Val Asp Trp Phe Thr Phe Tyr Lys Leu
                10                  15                  20 cct aaa aga caa aac aag gaa agt gga gag act ggg tta gag tac ctg     192
Pro Lys Arg Gln Asn Lys Glu Ser Gly Glu Thr Gly Leu Glu Tyr Leu
            25                  30                  35 tac cta gac tct aca act aga agc tgg agg aag agt gag caa cta atg     240
Tyr Leu Asp Ser Thr Thr Arg Ser Trp Arg Lys Ser Glu Gln Leu Met
        40                  45                  50 aat gac acc aag agt gtt ttg gga agg aca tta caa cag cta tat gaa     288
Asn Asp Thr Lys Ser Val Leu Gly Arg Thr Leu Gln Gln Leu Tyr Glu
    55                  60                  65 gca tat gcc tct aag agt aac aac aca gcc tat cta ata tac aat gat     336
Ala Tyr Ala Ser Lys Ser Asn Asn Thr Ala Tyr Leu Ile Tyr Asn Asp
```

```
                70                  75                  80                  85
gga gtc cct aaa cct gtg aat tac agc aga aag tat gga cac acc aaa           384
Gly Val Pro Lys Pro Val Asn Tyr Ser Arg Lys Tyr Gly His Thr Lys
                90                      95                      100 ggt tta ctg ctg tgg aac aga gtt caa ggg ttc tgg ctg att cat tcc           432
Gly Leu Leu Leu Trp Asn Arg Val Gln Gly Phe Trp Leu Ile His Ser
                105                     110                     115 atc cct cag ttt cct cca att ccg gaa gaa ggc tat gat tat cca ccc           480
Ile Pro Gln Phe Pro Pro Ile Pro Glu Glu Gly Tyr Asp Tyr Pro Pro
                120                     125                     130 aca ggg aga cga aat gga caa agt ggc atc tgc ata act ttc aag tac           528
Thr Gly Arg Arg Asn Gly Gln Ser Gly Ile Cys Ile Thr Phe Lys Tyr
        135                     140                     145 aac cag tat gag gca ata gat tct cag ctc ttg gtc tgc aac ccc aac           576
Asn Gln Tyr Glu Ala Ile Asp Ser Gln Leu Leu Val Cys Asn Pro Asn
150                     155                     160                     165 gtc tat agc tgc tcc atc cca gcc acc ttt cac cag gag ctc att cac           624
Val Tyr Ser Cys Ser Ile Pro Ala Thr Phe His Gln Glu Leu Ile His
                170                     175                     180 atg ccc cag ctg tgc acc agg gcc agc tca tca gag att cct ggc agg           672
Met Pro Gln Leu Cys Thr Arg Ala Ser Ser Ser Glu Ile Pro Gly Arg
                185                     190                     195 ctc ctc acc aca ctt cag tcg gcc cag gga caa aaa ttc ctc cat ttt           720
Leu Leu Thr Thr Leu Gln Ser Ala Gln Gly Gln Lys Phe Leu His Phe
                200                     205                     210 gca aag tcg gat tct ttt ctt gat ggc atc ttt gca gcc tgg atg gct           768
Ala Lys Ser Asp Ser Phe Leu Asp Gly Ile Phe Ala Ala Trp Met Ala
        215                     220                     225 caa cgg ctg aag aca cac ttg tta aca gaa acc tgg cag cga aaa aga           816
Gln Arg Leu Lys Thr His Leu Leu Thr Glu Thr Trp Gln Arg Lys Arg
230                     235                     240                     245 caa gag ctt cct tca aac tgc tcc ctt cct tac cat gtc tac aat ata           864
Gln Glu Leu Pro Ser Asn Cys Ser Leu Pro Tyr His Val Tyr Asn Ile
                250                     255                     260 aaa gca att aaa tta tca cga cac tct tat ttc agt tct tat caa gat           912
Lys Ala Ile Lys Leu Ser Arg His Ser Tyr Phe Ser Ser Tyr Gln Asp
                265                     270                     275 cat gcc aag tgg tgt att tcc caa aag ggc acc aaa aat cgc tgg aca           960
His Ala Lys Trp Cys Ile Ser Gln Lys Gly Thr Lys Asn Arg Trp Thr
                280                     285                     290 tgt att gga gac cta aat cgg agt cca cac caa gcc ttc aga agt gga          1008
Cys Ile Gly Asp Leu Asn Arg Ser Pro His Gln Ala Phe Arg Ser Gly
        295                     300                     305 gga ttc att tgt acc cag aat tgg caa att tac caa gca ttt caa gga          1056
Gly Phe Ile Cys Thr Gln Asn Trp Gln Ile Tyr Gln Ala Phe Gln Gly
310                     315                     320                     325 tta gta tta tac tat gaa agc tgt aag taa                                  1086
Leu Val Leu Tyr Tyr Glu Ser Cys Lys
                330
```

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide designed to act as sense primer
      for amplifying 3'-terminal of mouse DLAD cDNA.

<400> SEQUENCE: 5
aatgaatatg gtgaagctgt ggactgg                                             27

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide designed to act as antisense
      primer for amplifying 5'-terminal of mouse DLAD cDNA.

<400> SEQUENCE: 6
ccatcgttgt atattagata ggctgtg                                          27

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide designed to act as linker
      primer for amplifying 5'- and 3'-terminals of DLAD cDNA.

<400> SEQUENCE: 7
ccatcctaat acgactcact atagggc                                          27

<210> SEQ ID NO 8
<211> LENGTH: 52
<212> TYPE: DNA
<213> ORGANISM: Artificial Sequence
<220> FEATURE:
<223> OTHER INFORMATION: Oligonucleotide designed to act as primer
      for reverse transcription of mouse DLAD RNA.
<220> FEATURE:
<221> NAME/KEY: misc_feature
<222> LOCATION: (51)..(51)
<223> OTHER INFORMATION: "v" is g, a or c.
<220> FEATURE:
<221> NAME/KEY: misc_feature
<222> LOCATION: (52)..(52)
<223> OTHER INFORMATION: "n" is g, a, c or t.

<400> SEQUENCE: 8
ttctagaatt cagcggccgc tttttttttt tttttttttt tttttttttt vn              52

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide designed to act as sense
      primer for amplifying full length mouse DLAD cDNA.

<400> SEQUENCE: 9
ctcgagccac catgacagca aagcctctaa gaaca                                 35

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide designed to act as antisense
      primer for amplifying full length mouse DLAD cDNA.

<400> SEQUENCE: 10
ctcgagactt acagaaccca taacggagat                                       30

<210> SEQ ID NO 11
<211> LENGTH: 32
<212> TYPE: DNA
<213> ORGANISM: Artificial Sequence
<220> FEATURE:

```
<223> OTHER INFORMATION: Oligonucleotide designed to act as sense
      primer for amplifying coding sequence of DNase II signal peptide.

<400> SEQUENCE: 11
ctcgagccac catgatcccg ctgctgctgg ca                                   32

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide designed to act as antisense
      primer for amplifying coding sequence of DNase II signal peptide.

<400> SEQUENCE: 12
gcaggtcagg gcgccggc                                                   18

<210> SEQ ID NO 13
<211> LENGTH: 29
<212> TYPE: DNA
<213> ORGANISM: Artificial Sequence
<220> FEATURE:
<223> OTHER INFORMATION: Oligonucleotide designed to act as sense
      primer for amplifying coding sequence of DLAD lacking its signal
      peptide.

<400> SEQUENCE: 13
agctaggcgc cctctcatgc agaaatgaa                                       29

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide designed to act as sense
      primer for amplifying 3'-terminal of human DLAD cDNA.

<400> SEQUENCE: 14
aactgctccc ttccttacca tgtctac                                         27

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide designed to act as antisense
      primer for amplifying 5'-terminal of human DLAD cDNA.

<400> SEQUENCE: 15
gaaggcttgg tgtggactcc gatttag                                         27
```

DEOXYRIBONUCLEASE, GENE ENCODING SAME AND USE THEREOF

CROSS REFERENCE TO RELATED APPLICATIONS

This patent application is a divisional of U.S. patent application Ser. No. 10/670,863, filed on Sep. 25, 2003, which issued as U.S. Pat. No. 7,049,123 on May 23, 2006, and which is a divisional application of U.S. patent application Ser. No. 09/807,784, filed on Jul. 3, 2001, which issued as U.S. Pat. No. 6,653,118 B1 on Nov. 25, 2003.

TECHNICAL FIELD

This invention relates to a novel deoxyribonuclease capable of cleaving DNA independently from divalent cations under acidic conditions, a DNA encoding same and use of these for the prophylaxis and treatment of infectious diseases as well as for the treatment of cystic fibrosis.

BACKGROUND ART

The presence of various deoxyribonucleases (hereinafter referred to as DNase) in mammalian cells has been known. DNase II is one of the DNases studied most and catalyzes DNA hydrolysis reaction in the absence of divalent cations at acidic pH [in *The Enzymes* (Boyer, P. D., ed) 3rd Ed., Vol. 4, pp. 271-287 (1971), Academic Press, New York; *Arch. Biochem. Biophys.*, 300: 440-450 (1993)]. While the acid DNase activities are widely found in various animal tissues [*Biochim. Biophys. Acta*, 1119: 185-193 (1992); *J. Biol. Chem.*, 273: 2610-2616 (1998)], DNase II has been considered to be the sole enzyme responsible for the acid DNase activities. Because DNase II shows low organ specificity and is distributed ubiquitously, a possibility of DNase II playing an important biological role in the fundamental biological phenomena, such as DNA catabolism and apoptosis, has been suggested [*The Enzymes* (1971), supra; *Arch. Biochem. Biophys.*, 300: 440-450 (1993)].

Even though the enzymological properties of the DNase II isolated from different organisms are very similar, their physicochemical properties and molecular structures are strikingly different. For example, it is known that porcine DNase II is a complex protein consisting of unidentical subunits derived from its precursor protein, but DNase II derived from other animals are mostly single polypeptides [*J. Biol. Chem.*, 260: 10708-10713 (1985); *Biochem. Biophys. Res. Commun.*, 247: 864-869 (1998); *J. Biol. Chem.*, 251: 116-123 (1976); *Gene*, 215: 281-289 (1998)]. Furthermore, the apparent molecular weights of DNase II vary from 26.5 kDa to 45 kDa [*J. Biol. Chem.* (1976), supra; *Gene*, (1998), supra; *J. Biol. Chem.*, 247: 1424-1432 (1972); *Eur. J. Biochem.*, 202: 479-484 (1991)].

The diversity of acid DNases can be also appreciated from the subcellular localization. DNase II is considered to be localized in lysosomes [*J. Biol. Chem.* (1972), supra; *Biochim. Biophys. Acta*, 1007: 15-22 (1989)], but acid DNase activity is also found in nuclear fraction [*Arch. Biochem. Biophys.* (1993), supra; *Biochem. J.*, 136: 83-87 (1973)].

The reason for such molecular diversity of DNase II still remains unclear, but the aforementioned findings suggest the existence of a different acid DNase distinguishable from DNase II. In fact, the present inventors have identified and partially purified novel acid DNases (DNase α and DNase β) from the nuclear fraction of rat thymus (JP 8-187079 A). In view of the foregoing situation it is considered to be critical for the elucidation of the diversity of acid DNases to search other novel acid DNases and determine their characteristics.

In addition, DNase has been actively studied with the aim of applying same for the prophylaxis and treatment of various diseases. One of the clinical applications of DNase, which has been drawing particular attention in recent years, is an application to the treatment of cystic fibrosis (hereinafter sometimes to be also referred to as CF) [*Annu. Rev. Pharmacol. Toxicol.*, 35: 257-276 (1995); *Chest*, 107: 65-70 (1995)]. CF is a lethal hereditary disease caused by abnormal chloride ion channel of exocrine glands. In the Caucasian population, one in 2500 newborns suffers from this disease and one in 25 Caucasians is a carrier. About 90% of the CF patients die of respiratory insufficiency caused by intractable infection with *Pseudomonas aeruginosa* in the inferior airway in their 20's and 30's [*Curr. Opin. Pulm. Med.*, 6: 425-434 (1995)]. Phlegm that is accumulated in the airway to impair the respiratory function is caused by high concentration DNA released from the disrupted leukocytes infiltrating into the inflammatory site. Genentech, Inc. U.S. is selling a recombinant DNase I as a therapeutic agent for CF in Europe and America, which aims at removing the high molecular weight DNA accumulated in the lung, recovering the respiratory function and preventing infectious diseases [*Annu. Rev. Pharmacol. Toxicol.* (1995), supra; *Chest* (1995), supra]. DNase I not only degrades DNA, but also depolymerizes F-actin which is abundant in the sputum of CF patients. However, since the resulting monomeric G-actin strongly inhibits DNase I, DNase I is immediately inactivated. Actually, DNase I hardly shows any therapeutic effect. Some attempts have been made to produce a G-actin nonsensitive DNase I by genetic recombination, but satisfactory DNase has not been obtained yet [*Proc. Natl. Acad. Sci. USA*, 93: 8225-8229 (1996); *J. Biol. Chem.*, 273: 18374-18381 (1998)]. Thus, there is a demand on the identification of a novel G-actin nonsensitive DNase effective for the treatment of CF.

A second interest in the clinical application of DNase is that for the prophylaxis and treatment of infectious diseases. Some DNases are considered to play an important role in the biological defense mechanisms against infection with bacteria and viruses, based on degradation of foreign genomic DNAs. Accordingly, identification of the DNase involved in the prevention of infection in mammals, such as human, and utilization thereof as a medicament are expected to open a new possibility in the prophylaxis and treatment of infectious diseases.

It is therefore an object of the present invention to provide a novel acid DNase and clarify the characteristics of the enzyme, thereby providing critical information for the study of the molecular diversity of acid DNases. It is another object of the present invention to provide a novel G-actin nonsensitive DNase that can be effectively used as a therapeutic agent of CF. It is yet another object of the present invention to provide a novel DNase useful for the prophylaxis and treatment of infectious diseases.

DISCLOSURE OF THE INVENTION

In an attempt to accomplish the above-mentioned objects, the present inventors have conducted intensive studies, and succeeded in isolating cDNA clones containing an ORF encoding a novel protein homologous to human DNase II, from RNA derived from the liver of human, mouse or rat. Furthermore, it has been confirmed that this protein has an endonuclease activity capable of cleaving the DNA independently from divalent cations under acidic conditions, like DNase II, but is a novel acid DNase distinguishable from DNase II in the capability of exerting the DNase activity even in the neutral pH range and the sensitivity against divalent metallic ion inhibitors, as a result of the analysis of the physicochemical and enzymological characteristics of the protein obtained by culturing a host cell transformed with an expression vector containing the cDNA clone and purifying the recombinant protein. Then, the present inventors have designated the novel acid DNase as DLAD (DNase II-Like Acid DNase). The present inventors have also demonstrated that this enzyme has a high possibility of making an effective therapeutic agent of CF by confirming that the DLAD activity is not inhibited by G-actin. Moreover, the present inventors have confirmed a high possibility of the DLAD having a preventive effect on viral infectious diseases, which resulted in the completion of the present invention.

Accordingly, the present invention provides the following.
(1) A DNase which is an endonuclease capable of cleaving DNA independently from divalent cations under acidic conditions and having the following properties:
(1) active pH range: ca. 4.0 to ca. 7.6
(2) DNA cleavage mode: 3'-P/5'-OH end forming type
(3) sensitivity against inhibitors:
(i) inhibited by $Zn^{2+}$
(ii) not inhibited by G-actin
(2) The DNase of (1) above, further having the following properties:
(1) optimal pH: ca. 5.2
(2) molecular weight: ca. 55 kDa as a post-translational modification product (SDS-PAGE)
(3) localization: present in cytoplasm and extracellularly, rich in cytoplasm
(4) tissue specificity: specifically expressed in the liver.
(3) A DNase having the following polypeptide (a) or (b):
(a) a polypeptide consisting of an amino acid sequence of amino acid Nos. 1 to 332 of the amino acid sequence shown in Sequence Listing, SEQ ID NO: 1
(b) a polypeptide having the same amino acid sequence of (a) above, except that one to several amino acids are deleted, substituted, inserted, added or modified, wherein a mature protein has an endonuclease activity capable of cleaving a DNA independently from divalent cations in a pH range of from ca. 4.0 to ca. 7.6.
(4) The DNase of any of (1) to (3) above, wherein a primary translation product contains an N terminal signal peptide sequence, preferably an amino acid sequence of the amino acid Nos. −22 to −1 of the amino acid sequence shown in Sequence Listing, SEQ ID NO: 1.
(5) The DNase of any of (1) to (4) above, which is derived from a mammal, preferably mouse.
(6) A DNase having the following polypeptide (a) or (b):
(a) a polypeptide consisting of an amino acid sequence of the amino acid Nos. 1 to 334 of the amino acid sequence shown in Sequence Listing, SEQ ID NO: 3.
(b) a polypeptide having the same amino acid sequence of (a) above, except that one to several amino acids are deleted, substituted, inserted, added or modified, wherein a mature protein has an endonuclease activity capable of cleaving a DNA independently from divalent cations in a pH range of from ca. 4.0 to ca. 7.6.
(7) The DNase of any of (1), (2) and (6) above, wherein a primary translation product contains an N terminal signal sequence, preferably an amino acid sequence of the amino acid Nos. −27 to −1 of the amino acid sequence shown in Sequence Listing, SEQ ID NO: 3.
(8) The DNase of (1), (2), (6) or (7) above, which is derived from a mammal, preferably human.
(9) A DNA encoding the DNase of any of (1) to (8) above.
(10) A DNA consisting of the following nucleotide sequence (a) or (b):
(a) a nucleotide sequence of the nucleotide Nos. 279 to 1274 of the nucleotide sequence shown in Sequence Listing, SEQ ID NO: 2
(b) a nucleotide sequence capable of being hybridized to the nucleotide sequence of (a) above under stringent conditions, which encodes a DNase having an endonuclease activity capable of cleaving DNA independently from divalent cations in a pH range of from ca. 4.0 to ca. 7.6.
(11) A DNA consisting of the following nucleotide sequence (a) or (b):
(a) a nucleotide sequence of the nucleotide Nos. 213 to 1274 of the nucleotide sequence shown in Sequence Listing, SEQ ID NO: 2
(b) a nucleotide sequence capable of being hybridized to the nucleotide sequence of (a) above under stringent conditions, which encodes a primary translation product of a DNase whose mature protein has an endonuclease activity capable of cleaving DNA independently from divalent cations in a pH range of from ca. 4.0 to ca. 7.6.
(12) The DNA of (10) or (11) above, which is derived from a mammal, preferably mouse.
(13) A DNA consisting of the following nucleotide sequence (a) or (b):
(a) a nucleotide sequence of the nucleotide Nos. 82 to 1083 of the nucleotide sequence shown in Sequence Listing, SEQ ID NO: 4
(b) a nucleotide sequence capable of being hybridized to the nucleotide sequence of (a) above under stringent conditions, which encodes a DNase having an endonuclease activity capable of cleaving DNA independently from divalent cations in a pH range of from ca. 4.0 to ca. 7.6.
(14) A DNA consisting of the following nucleotide sequence (a) or (b):
(a) a nucleotide sequence of the nucleotide Nos. 1 to 1083 of the nucleotide sequence shown in Sequence Listing, SEQ ID NO: 4.
(b) a nucleotide sequence capable of being hybridized to the nucleotide sequence of (a) above under stringent conditions, which encodes a primary translation product of a DNase whose mature protein has an endonuclease activity capable of cleaving DNA independently from divalent cations in a pH range of from ca. 4.0 to ca. 7.6.
(15) The DNA of (13) or (14) above, which is derived from a mammal, preferably human.
(16) A recombinant vector containing the DNA of any of (9) to (15) above.
(17) An expression vector containing the DNA of any of (9) to (15) above and a promoter operably linked to said DNA.
(18) A transformant obtained by transforming a host cell with the expression vector of (17) above.
(19) A method for producing the DNase of any of (1) to (8) above, which comprises culturing the transformant of (18) above in a medium and recovering said DNase from the resulting culture.
(20) A pharmaceutical composition containing the DNase of any of (1) to (8) above, the expression vector of (17) above or the transformant of (18) above as an active ingredient.
(21) The pharmaceutical composition of (20) above, which is for the prophylaxis and treatment of infectious diseases or for the treatment of cystic fibrosis.

Inasmuch as the DLAD of the present invention is an acid DNase that expresses the activity in a broad pH range of from acidic to neutral pHs independently from divalent cations, and is resistant to G-actin, it is useful for degrading a high concentration DNA contained in the sputum of CF patients, improving the respiratory function.

Furthermore, because the DLAD of the present invention can suppress the intracellular expression of foreign genes, it also provides a useful means for the prophylaxis and treatment of infectious diseases, such as viral infection.

BEST MODE FOR CARRYING OUT THE INVENTION

Figure 1:
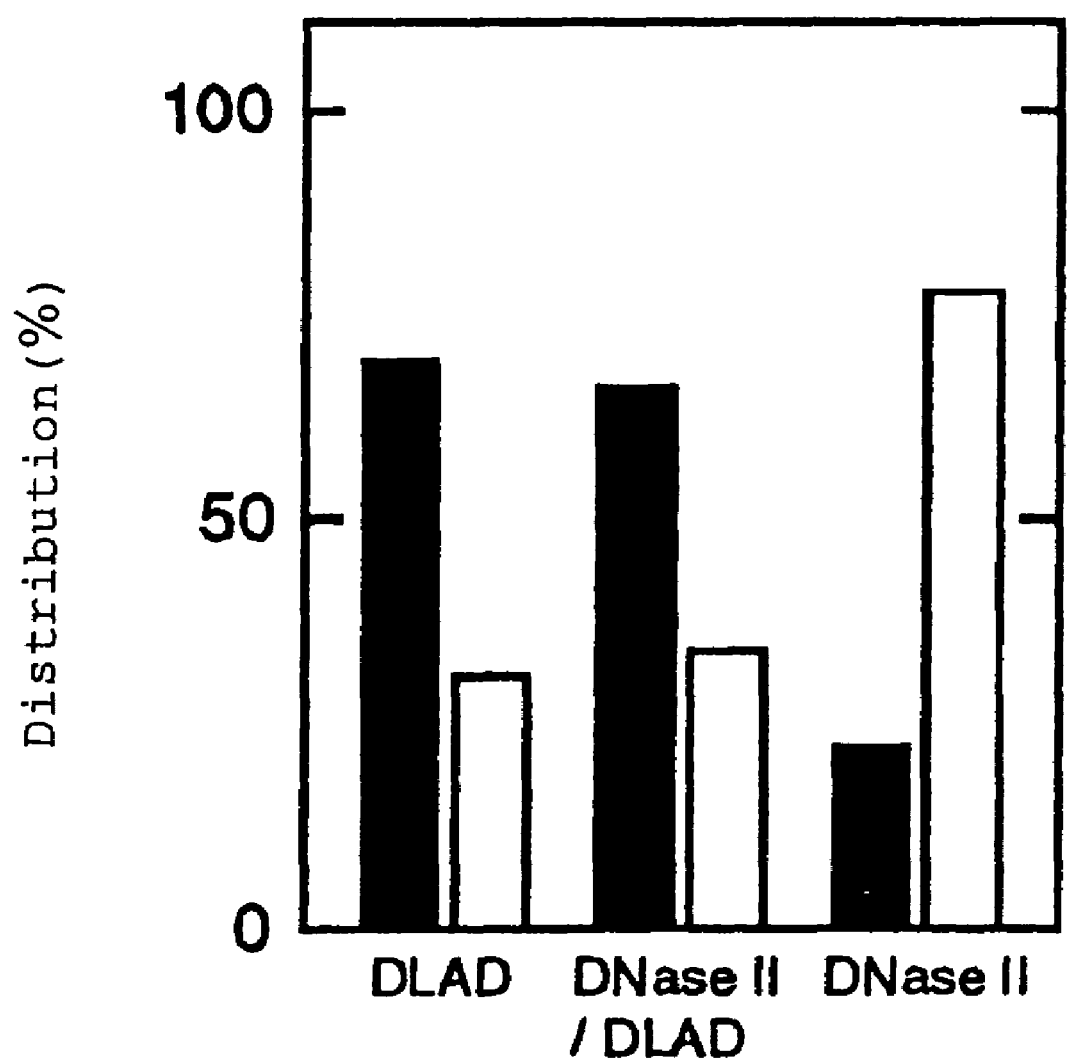
FIG. 1 shows an intracellular/extracellular (medium) presence ratio (% of the total) of each protein in HeLa S3 cells engineered to express DLAD, DNase II signal-DLAD chimeric protein or DNase II, wherein a black line shows intracellular presence and a white line shows extracellular presence.

The DLAD of the present invention is similar to DNase II, which is a known acid DNase, in that it has an endonuclease activity that hydrolyzes DNA to generate 3'-P/5'-OH termini under acidic conditions independently from divalent cations. However, DLAD is extremely characteristic in that it exerts DNase activity over a wide pH range of from pH ca. 4.0 to ca. 7.6, whereas DNase II shows activity only in a pH range of not more than ca. 5.6. The pH range preferable for the DLAD activity is from ca. 4.4 to ca. 6.8, and the optimal pH is about 5.2.

DLAD is also characteristically different from DNase II in the sensitivity to divalent metal ions. To be specific, DLAD is significantly sensitive to $Zn^{2+}$ as compared with $Co^{2+}$, $Ni^{2+}$ and the like, whereas $Co^{2+}$, $Ni^{2+}$, $Cu^{2+}$, $Zn^{2+}$ and the like influence DNase II activity to almost the same level.

The DLAD of the present invention is not inhibited by G-actin, unlike DNase I, etc.

The DLAD of the present invention is not particularly limited as long as it has the above-mentioned characteristics, and the origin of DLAD is not limited, either. Thus, it encompasses not only those originated from naturally occurring organisms but also spontaneous or artificial mutants or those derived from transformants obtained by introducing a heterologous (i.e., foreign) DLAD gene. Preferably, it includes DLAD derived from mammals, such as human, bovine, porcine, horse, monkey, sheep, goat, canine, feline, rabbit, mouse, rat, guinea pig and the like. Those derived from human, bovine, porcine, mouse and rat are particularly preferable.

The DLAD of the present invention can have various molecular weights by changing the amino acid composition or by glycosylation, and preferably has a molecular weight of about 38 to 39 kDa (calculated) when it is an unglycosylated mature polypeptide chain, and about 55 kDa (SDS-PAGE) when it is a glycosylated mature protein (post-translational modification product). When DLAD is translated as a precursor containing a signal peptide sequence, it preferably has a molecular weight of about 41 to 42 kDa when it is a primary translation product.

In an embodiment of the present invention, DLAD is distributed both extracellularly and in cytoplasm. More specifically, DLAD is present mainly in cytoplasm, and shows a presence ratio different from that of DNase II. In this embodiment, as is expected from additional extracellular secretion, the primary translation product of DLAD contains a signal peptide sequence at its N terminus. The signal peptide is not particularly limited as long as it is recognized and cleaved by a signal peptidase in endoplasmic reticulum, resulting in a mature DLAD protein. Examples thereof include an amino acid sequence of the amino acid Nos. −22 to −1 of the amino acid sequence shown in Sequence Listing, SEQ ID NO: 1, an amino acid sequence of the amino acid Nos. −27 to −1 of the amino acid sequence shown in Sequence Listing, SEQ ID NO: 3, and an amino acid sequence obtained by deleting, substituting, inserting or adding one to several amino acids of these amino acid sequences as long as the property of a signal sequence is generally understood to be retained. Signal sequences of other secretory proteins, such as DNase II, are also preferable.

It is not particularly limited where in the substructure of cytoplasm a cytoplasmic DLAD is localized, but it is preferably localized in one or more organelles in an acidic environment, such as lysosomes and peroxysomes.

The expression of the DLAD of the present invention is highly restricted to that in the liver, making a sharp contrast with DNAse II which is low in organ specificity.

In a preferable embodiment of the present invention, DLAD is a polypeptide consisting of an amino acid sequence of the amino acid Nos. 1 to 332 of the amino acid sequence shown in Sequence Listing, SEQ ID NO: 1 or a polypeptide consisting of an amino acid sequence of the amino acid Nos. 1 to 334 of the amino acid sequence shown in Sequence Listing, SEQ ID NO: 3, or a polypeptide which consists of the same amino acid sequence of these, except that one to several amino acids are deleted, substituted, inserted, added or modified, and which has an endonuclease activity capable of cleaving DNA in a pH range of from ca. 4.0 to ca. 7.6 independently from divalent cations.

The DLAD of the present invention can be obtained by appropriately employing (1) a method including extraction and purification from the cells or tissues, that produce this enzyme, as a starting material, (2) a method including chemical synthesis or (3) a method including purification from the cells engineered to express DLAD by genetic recombination techniques, or the like.

For example, the isolation and purification of DLAD from a naturally occurring DLAD-producing tissue can be carried out as follows. A mammalian tissue (e.g., a liver tissue section from human, mouse, rat, etc.) is homogenized in a suitable extraction buffer, ultrasonicated or treated with a surfactant to give a cell extract, and purified by a suitable combination of separation techniques conventionally utilized for separation and purification of proteins. Examples of the separation technique include methods utilizing difference in solubility, such as salting out and solvent precipitation, methods utilizing difference in molecular weight, such as dialysis, ultrafiltration, gel filtration, non-denatured polyacrylamide gel electrophoresis (PAGE) and sodium dodecyl sulfate-polyacrylamide gel electrophoresis (SDS-PAGE), methods utilizing charge, such as ion exchange chromatography and hydroxyapatite chromatography, methods utilizing specific affinity, such as affinity chromatography, methods utilizing difference in hydrophobicity, such as reversed phase high performance liquid chromatography, methods utilizing difference in isoelectric point, such as isoelecric focusing, and the like.

Alternatively, DLAD can be obtained by culturing mammal-derived cultured cells, for example, cultured cells derived from liver cells of human, mouse, rat and the like, in a suitable liquid medium and purifying from the obtained culture supernatant by the above-mentioned conventional protein separation techniques.

The production of DLAD by chemical synthesis can be carried out by, for example, synthesizing the whole or partial sequence based on an amino acid sequence (amino acid Nos. 1 to 332) shown in Sequence Listing, SEQ ID NO: 1 or an amino acid sequence (amino acid Nos. 1 to 334) shown in Sequence Listing, SEQ ID NO: 3 using a peptide synthesizer and renaturing the obtained polypeptide under suitable renaturation conditions.

The DLAD of the present invention is preferably produced by cloning a DNA encoding the protein, and isolating and purifying from the culture of a transformant containing an expression vector carrying the DNA.

The cloning of an enzyme gene is typically performed as follows. First, a desired enzyme is completely or partially purified from cells or tissues producing said enzyme using the above-mentioned means, followed by Edman method to determine its N terminal amino acid sequence. Furthermore, the enzyme is partially degraded with proteases or chemical substances that cleave a peptide in a sequence specific manner, and the amino acid sequence of the obtained oligopeptide is determined in the same manner by Edman method. The oligonucleotides having the nucleotide sequences corresponding to the determined amino acid sequences are synthesized, and using them as probes, a DNA encoding said enzyme is cloned from a cDNA or genomic DNA library prepared from the cells or tissues that produce said enzyme by colony (or plaque) hybridization method.

Alternatively, an antibody against the enzyme is produced according to a conventional method using, as an antigen, the entirety or a part of the completely or partially purified enzyme, and a DNA encoding said enzyme can be cloned by antibody screening method from a cDNA or genomic DNA library prepared from the cells or tissues, that produce this enzyme.

When a gene encoding an enzyme, whose enzymological properties are similar to those of the enzyme of interest, is known, a DNA encoding said enzyme can be cloned by searching EST (Expressed Sequence Tag) clones of mammals, such as human, mouse and rat, registered on generally available databases, such as EMBL and GenBank, extracting a clone that shows homology to the nucleotide sequence of the known gene, producing probes as mentioned above, based on the nucleotide sequence of the extracted EST clone, and carrying out colony (or plaque) hybridization. In the case of the DLAD of the present invention, an EST clone, which is a fragment of cDNA encoding DLAD, can be found by a homology search using a nucleotide sequence encoding DNase II derived from mammals such as human.

Alternatively, RACE method can be used to obtain a cDNA clone more rapidly and easily. To be specific, an EST clone corresponding to a part of the DLAD gene is extracted as mentioned above, oligonucleotides homologous to the partial nucleotide sequences of sense and antisense strands of said EST clone are respectively synthesized. Using each oligonucleotide and an appropriate adaptor primer as a pair of PCR primers, 5' and 3' RACE reactions are carried out, and each amplification fragment is ligated by a method using a restriction enzyme and a ligase to give a full length cDNA clone.

The nucleotide sequence of the DNA obtained as mentioned above can be determined using known sequencing techniques such as Maxam-Gilbert method and dideoxy termination method.

The DNA encoding DLAD of the present invention is preferably a DNA encoding an amino acid sequence of the amino acid Nos. 1 to 332 of the amino acid sequence shown in Sequence Listing, SEQ ID NO: 1 or an amino acid sequence of the amino acid Nos. 1 to 334 of the amino acid sequence shown in Sequence Listing, SEQ ID NO: 3, or the same amino acid sequences of these, except that one to several amino acids are deleted, substituted, inserted, added or modified, wherein a protein consisting of said mutated amino acid sequence has an endonuclease activity capable of cleaving DNA in a pH range of from ca. 4.0 to ca. 7.6 independently from divalent cations. More preferably, the DNA encoding DLAD of the present invention is one which consists of a nucleotide sequence of the nucleotide Nos. 279 to 1274 of the nucleotide sequence shown in Sequence Listing, SEQ ID NO: 2 or a nucleotide sequence of the nucleotide Nos. 82 to 1083 of the nucleotide sequence shown in Sequence Listing, SEQ ID NO: 4, or a nucleotide sequence capable of being hybridized to these nucleotide sequences under stringent conditions, wherein the mutated nucleotide sequence encodes a protein having an endonuclease activity capable of cleaving DNA in a pH range of from ca. 4.0 to ca. 7.6, independently from divalent cations.

The DNA encoding DLAD of the present invention is preferably one further containing a nucleotide sequence encoding a signal peptide sequence at the 5' terminus of the nucleotide sequence as mentioned above. More preferably, the DNA encoding DLAD of the present invention consists of the nucleotide sequence of the nucleotide Nos. 213 to 1274 of the nucleotide sequence shown in Sequence Listing, SEQ ID NO: 2 or the nucleotide sequence of the nucleotide Nos. 1 to 1083 of the nucleotide sequence shown in Sequence Listing, SEQ ID NO: 4, or a nucleotide sequence capable of being hybridized to these nucleotide sequence under stringent conditions, wherein the mutated nucleotide sequence encodes a primary translation product of a protein having an endonuclease activity capable of cleaving DNA in a pH range of from ca. 4.0 to ca. 7.6, independently from divalent cations.

In the context of the present invention, the "stringent conditions" means those under which a DNA having not less than about 60% homology to the nucleotide sequence can be hybridized. The stringency can be controlled by appropriately varying salt concentrations and temperatures of the hybridization reaction and washing.

The DNA encoding DLAD of the present invention can be a DNA chemically synthesized based on the nucleotide sequence of the nucleotide Nos. 279 to 1274 or the nucleotide Nos. 213 to 1274 of the nucleotide sequence shown in Sequence Listing, SEQ ID NO: 2, or the nucleotide sequence of the nucleotide Nos. 82 to 1083 or the nucleotide Nos. 1 to 1083 of the nucleotide sequence shown in Sequence Listing, SEQ ID NO: 4.

The present invention also provides a recombinant vector containing a DNA encoding DLAD of the invention. The inventive recombinant vector is not particularly limited as long as it can be maintained by replication or autonomously replicated within various host cells, such as prokaryotic cells and/or eukaryotic cells, and encompasses plasmid vectors, viral vectors and the like. The recombinant vectors can be easily prepared by ligating the above-mentioned DNA encoding DLAD to known cloning vectors or expression vectors available in this technical field, using suitable restriction enzymes and a ligase, and further, linkers or adaptors as necessary. Examples of such vectors include pBR322, pBR325, pUC18, pUC19 etc. as a plasmid derived from *Escherichia coli*; pSH19, pSH15 etc. as a plasmid derived from yeast; and pUB110, pTP5, pC194 etc. as a plasmid derived from *Bacillus subtilis*. Examples of the viruses include bacteriophages such as λ phage, and animal and insect viruses such as parvovirus (SV40, bovine papilloma virus (BPV) etc.), retrovirus (Moloney murine leukemia virus (MoMuLV) etc.), adenovirus (AdV), adeno-associated virus (AAV), vacciniavirus, vaculovirus, and the like.

Particularly, the present invention provides a DLAD expression vector in which a DNA encoding DLAD is placed under the control of a promoter functional in a desired host cell. The vector to be used is not particularly limited as long as it contains a promoter region, which is capable of functioning in various host cells such as prokaryotic and/or eukaryotic cells and regulating the transcription of a gene located at its downstream (e.g., when the host is *Escherichia coli*, trp promoter, lac promoter, lecA promoter, etc., when the host is *Bacillus subtilis*, SPO1 promoter, SPO2 promoter, penP promoter, etc., when the host is yeast, PHO5 promoter, PGK promoter, GAP promoter, ADH promoter, etc., and when the host is mammalian cell, viral promoters such as SV40 early promoter, MoMuLV long terminal repeat, adenovirus early promoter, etc.), and a termination signal of the transcription of said gene, i.e., terminator region, wherein the promoter region and the terminator region are ligated via a sequence containing at least one restriction enzyme recognition site, preferably unique restriction site that cleaves the vector only at this site. However, it is preferable that it further contain a selectable marker gene for selecting transformants (e.g., a gene imparting resistance to a drug such as tetracycline, ampicillin, kanamycin, hygromycin and phosphinothricin, a gene complementing auxotrophic mutation etc.). Moreover, when the DNA encoding DLAD to be inserted does not contain an initiation codon or a termination codon, a vector, which contains an initiation codon (ATG or GTG) and a termination codon (TAG, TGA or TAA) at the downstream of the promoter and the upstream of the terminator, respectively, is preferably used.

When bacteria is used as a host cell, in general, the expression vector needs to contain a replicable unit which allows autonomous replication in the host cell, in addition to the above-mentioned promoter region and terminator region. The promoter region also contains an operator and Shine-Dalgarno (SD) sequence near the promoter.

When a yeast, animal cell or insect cell is used as a host cell, the expression vector preferably further contains enhancer sequences, non-translated regions on the 5'-side and 3'-side of DLAD mRNA, a polyadenylation site, and the like.

When DLAD is secreted into a culture medium of the transformant or proper glycosylation of the mature DLAD protein is desired but DNA encoding DLAD to be inserted does not have a sequence encoding signal peptide, a secretory expression vector, further containing a suitable signal codon following an initiation codon, is preferably used as a vector.

When the DNA encoding DLAD of the present invention is isolated from a genomic DNA and obtained together with its native promoter and terminator regions, the expression vector of the present invention can be prepared by inserting the DNA into a suitable site of a known cloning vector which can be maintained by replication or which can be autonomously replicated in a desired host cell. Since DLAD is expressed in a liver-specific manner in a preferable embodiment of the present invention, the expression vector constructed as mentioned above can be preferably employed when a tissue- or organ-specific expression of DLAD is desired (e.g., in the treatment of a CF patient with hepatic duct occlusion).

The present invention also provides a transformant obtained by transforming a host cell with the above-mentioned DLAD expression vector.

The host cell to be used in the invention is not particularly limited as long as it is capable of adapting to the above-mentioned expression vector and can be transformed therewith, and is exemplified by various cells such as naturally occurring cells or artificially established mutant or recombinant cells conventionally used in the technical field of the present invention [e.g., bacteria (*Escherichia coli*, *Bacillus subtilis*, lactobacillus etc.), yeast (*Saccharomyces, Pichia, Kluyveromyces* etc.), animal cell and insect cell]. In view of the use of DLAD as a medicament to be mentioned below, the host cells are preferably mammalian cells, particularly the cells derived from human, monkey, mouse, rat, hamster etc., especially human-derived cells. To be specific, exemplified are mouse-derived cells (COP, L, C127, Sp2/0, NS-1, NIH3 and T3), rat-derived cells, hamster-derived cells (BHK and CHO), monkey-derived cells (COS1, COS3, COS7, CV1 and Vero) and human-derived cells (HeLa, diploid fibroblast-derived cells, myeloma cells and Namalwa).

The expression vector can be introduced into a host cell using a method conventionally known. For example, the method of Cohen et al. [*Proc. Natl. Acad. Sci. USA.*, 69, 2110 (1972)], protoplast method [*Mol. Gen. Genet.*, 168, 111 (1979)] and competent method [*J. Mol. Biol.*, 56, 209 (1971)] can be used for bacteria; the method of Hinnen et al. [*Proc. Natl. Acad. Sci. USA.*, 75, 1927 (1978)] or Lithium method [*J. Bacteriol.*, 153, 163 (1983)] can be used for yeast; the method of Graham [*Virology*, 52, 456 (1973)] can be used for animal cell; and the method of Summers et al. [*Mol. Cell. Biol.*, 3, 2156-2165 (1983)] can be used for insect cell, for transformation.

The DLAD of the present invention can be produced by culturing a transformant containing the DLAD expression vector prepared as mentioned above in a medium, and recovering DLAD from the resulting culture.

The medium to be used preferably contains carbon source and inorganic or organic nitrogen source necessary for the growth of host cell (transformant). Examples of the carbon source include glucose, dextran, soluble starch and sucrose; examples of the inorganic or organic nitrogen source include ammonium salts, nitrates, amino acids, corn steep liquor, peptone, casein, meat extract, soybean lees, potato extract solution and the like. Where desired, other nutrient sources such as inorganic salts (e.g., calcium chloride, sodium dihydrogenphosphate and magnesium chloride), vitamins and antibiotics (e.g., tetracycline, neomycin, ampicillin and kanamycin) may be added.

Culture is performed by a method known in this field. Specific examples of the medium and culture conditions to be used depending on the host cell are shown in the following, which should not be construed as limiting the culture conditions of the invention.

When the host is bacteria, actinomyces, yeast or fungus, a liquid medium containing the aforesaid nutrient sources is suitable, with preference given to a medium having a pH of 5 to 8. When the host is *Escherichia coli*, preferable medium includes LB medium and M9 medium [Miller. J., *Exp. Mol. Genet*, p. 431, Cold Spring Harbor Laboratory, New York (1972)]. In this case, culture can be typically performed at 14° C. to 43° C. for about 3 to 24 hr with aeration and agitation as necessary. When the host is *Bacillus subtilis*, culture can be typically performed at 30° C. to 40° C. for about 16 to 96 hr with aeration and agitation as necessary. When the host is yeast, examples of the medium include Burkholder minimum medium [Bostian. K. L. et al., *Proc. Natl. Acad. Sci. USA,* 77, 4505 (1980)], and pH is preferably 5 to 8. Culture can be typically performed at 20° C. to 35° C. for about 14 to 144 hr with aeration and agitation as necessary.

When the host is animal cell, examples of the medium include minimum essential medium (MEM) containing about 5 to 20% fetal calf serum [*Science,* 122, 501 (1952)], Dulbecco's modified minimum essential medium (DMEM) [*Virology,* 8, 396 (1959)], RPMI1640 medium [*J. Am. Med. Assoc.,* 199, 519 (1967)], 199 medium [*Proc. Soc. Exp. Biol. Med.,* 73, 1 (1950)] and the like. The pH of the medium is preferably about 6 to 8. Culture is typically performed at 30° C. to 40° C. for about 15 to 72 hr with aeration and agitation as necessary.

When the host is an insect cell, examples of the medium include Grace's medium containing fetal calf serum [*Proc. Natl. Acad. Sci. USA,* 82, 8404 (1985)], and pH is preferably about 5 to 8. Culture is typically performed at 20° C. to 40° C. for about 15 to 100 hr with aeration and agitation as necessary.

The DLAD can be purified by an appropriate combination of various separation techniques conventionally used, according to the fractions having DLAD activity. In a preferable embodiment of the invention, DLAD is present both in cytoplasm and extracellularly (i.e., in medium).

The DLAD present in the medium in the culture can be obtained by centrifuging or filtering the culture to give a culture supernatant (filtrate) and applying the culture supernatant to known separation methods (e.g., salting out, solvent precipitation, dialysis, ultrafiltration, gel filtration, non-denatured PAGE, SDS-PAGE, ion exchange chromatography, hydroxylapatite chromatography, affinity chromatography, reversed-phase high performance liquid chromatography and isoelectric focusing), as appropriately selected.

The DLAD present in the cytoplasm can be isolated and purified by centrifuging or filtering the culture to harvest cells, suspending the cells in a suitable buffer, disrupting (lysing) the cells and organelle membranes by, for example, ultrasonication, lysozyme treatment, freeze-thawing, osmotic shock and/or treatment with surfactant such as Triton X-100, removing the debris by centrifugation or filtration to give a soluble fraction, and treating the soluble fraction according to the methods mentioned above.

As a means for obtaining the recombinant DLAD rapidly and easily, preferably exemplified is a method which comprises adding a DNA sequence encoding an amino acid sequence capable of adsorbing to a metal ion chelate (e.g., an sequence consisting of basic amino acids such as histidine, arginine or lysine, preferably histidine) to a certain region (preferably C terminus) of the DLAD coding sequence by gene manipulation, allowing expression within a host cell, and recovering DLAD from the DLAD active fraction in the cell culture by separation utilizing its affinity for a carrier immobilizing said metal ion chelate. The DNA sequence encoding an amino acid sequence capable of adsorbing to a metal ion chelate can be introduced into the DLAD coding sequence by, for example, performing PCR amplification using a hybrid primer comprising said DNA sequence linked to the nucleotide sequence encoding the C terminal amino acid sequence of DLAD, in the process of cloning DNA encoding DLAD, or by inserting the DNA encoding DLAD in frame into an expression vector containing said DNA sequence before the termination codon. The metal ion chelate adsorbent to be used for purification is prepared by bringing a solution containing a transition metal (e.g., divalent ion of cobalt, copper, nickel or iron, or trivalent ion of iron or aluminum, preferably divalent ion of cobalt or nickel) into contact with a ligand (e.g., a matrix onto which iminodiacetate (IDA) group, nitrilotriacetate (NTA) group or tris(carboxymethyl)ethylenediamine (TED) group is attached) to allow binding thereof with the ligand. The matrix part of the chelate adsorbent is not particularly limited as long as it is a conventional insoluble carrier.

The present invention provides a pharmaceutical composition containing the inventive DLAD, DLAD expression vector or transformant expressing DLAD as an active ingredient, specifically an agent for the treatment of chronic obstructive diseases (in particular cystic fibrosis) caused by the accumulation of high concentration DNA and an agent for the prophylaxis and treatment of infectious diseases caused by viruses and the like.

DNase I conventionally used for treating CF requires divalent cations for the expression of activity. However, it is speculated that the concentration of divalent cations in lung cysts is not sufficiently high to allow expression of activation of DNase I. It is also considered that the pH in the inflammatory lesions in lung cysts inclines from neutral to acidic, though the optimal pH of DNase I is about 7.1. Furthermore, due to the fatal property that DNase is inhibited by G-actin present in large amounts in the sputum of CF patients, DNase I is almost ineffective as an agent for treating CF. In contrast, the DLAD of the present invention is capable of cleaving DNA under acidic conditions independently from divalent cations. Furthermore, the DLAD of the invention has excellent properties for exhibiting a high DNase activity in the inflammatory lesions in lung cysts of CF patients, in that it is not inhibited by G-actin, it does not require any cofactor for the expression of its activity, and it can exhibit its activity even in the neutral pH range.

DLAD has a high homology to FP-CEL1 [*J. Virol.,* 72: 6742-6751 (1998)], which is a DNase II-related protein derived from fowlpox virus (FWPV). It is considered that, when a virus enters a cell infected with FWPV, the FWPV-derived DLAD homolog cleaves a DNA of the virus, thereby to exclude the competitive virus [*J. Virol.* (1998), supra]. Therefore, DLAD can also enhance the defensive function of a body against infections with virus etc., and is effective for the prophylaxis and treatment of infectious diseases. The infectious diseases that can be prevented or treated are not particularly limited, and exemplified by those caused by hepatitis A, B and C viruses, human immunodeficiency virus, influenza virus and herpes virus.

The administration subject of the inventive pharmaceutical composition is not particularly limited as long as it is an animal in need of the treatment of a chronic obstructive disease caused by the accumulation of high concentration of DNA, or the prophylaxis and treatment of an infectious disease caused by a virus or the like. It is preferably a mammal, more preferably a mammal such as human, monkey, bovine, horse or porcine, especially human.

The pharmaceutical composition of the present invention containing a DLAD protein as an active ingredient can be formulated by admixing DLAD with a pharmaceutically acceptable carrier to give a liquid preparation, powder, granule, tablet, capsule, syrup, injection, aerosol or the like, and can be administered orally or parenterally.

The pharmaceutically acceptable carrier may include, but not limited to, excipients (e.g., sucrose, starch, mannitol, sorbit, lactose, glucose, cellulose, talc, calcium phosphate, calcium carbonate etc.), binding agents (e.g., cellulose, methyl cellulose, hydroxypropylcellulose, polypropylpyrrolidone, gelatin, gum arabic, polyethylene glycol, sucrose, starch etc.), disintegrants (e.g., starch, carboxymethylcellulose, hydroxypropyl-starch, sodium glycol-starch, sodium bicarbonate, calcium phosphate, calcium citrate etc.), lubricants (e.g. magnesium stearate, aerosil, talc, sodium laurylsulfate etc.), flavors (e.g., citric acid, mentol, ammonium salt of glycyrrhizin, glycine, orange powders etc.), preservatives (e.g., sodium benzoate, sodium bisulfite, methylparaben, propylparaben etc.), stabilizers (e.g., citric acid, sodium citrate, acetic acid, etc.), suspending agents (e.g., methyl cellulose, polyvinylpyrrolidone, aluminum stearate etc.), dispersing agents (e.g., surfactant etc.), diluents (e.g., water, physiological saline, orange juice etc.) and base waxes (e.g., cacao butter, polyethylene glycol, white kerosine etc.).

Preferably, the pharmaceutical composition containing DLAD protein as an active ingredient is a preparation for oral preparation, an injection or an aerosol preparation.

Preparations suitable for oral administration are liquid obtained by dissolving an effective amount of DLAD in diluents such as water, physiological saline and orange juice, capsule, sachet or tablet containing an effective amount of DLAD as solid or granule, suspension containing an effective amount of DLAD suspended in an appropriate dispersion medium, and emulsion prepared by suspending a solution containing an effective amount of DLAD dissolved in an appropriate dispersion medium and emulsifying the suspension.

The aerosol preparation may include one in which DLAD is compressed with dichlorodifluoromethane, propane or nitrogen and a non-compressed preparation such as nebulizer and atomizer, and can be administered by inhalation or spraying into airways and the like.

Preparations suitable for parenteral administration include aqueous and non-aqueous isotonic sterile injectable liquids, which can contain antioxidant, buffer, bacteriostat and isotonicity agent and the like, and aqueous and non-aqueous sterile suspensions, which can contain suspending agent, solubilizer, thickener, stabilizer, preservative and the like. The DLAD preparations can be sealed in unit-dose or multi-dose containers such as ampoules or vials. It is also possible to lyophilize (freeze-dry) DLAD with a pharmaceutically acceptable carrier and preserved in the form that requires dissolving or suspending in an appropriate sterile vehicle immediately prior to use.

The dose of the pharmaceutical composition containing the DLAD protein of the invention varies depending upon the kind of disease to be prevented or treated, the progress of the disease, and the animal species, drug-tolerance, weight and age of the administration subject, which is typically 1 to 10,000 I.U./kg body weight, preferably 10 to 1,000 I.U./kg body weight, daily for an adult, which can be administered in a single dose or several doses.

The present invention also provides a pharmaceutical composition containing the DLAD expression vector of the present invention as an active ingredient. Since the treatment of CF using DNases is not fundamental but suppressive, continuous supply of DLAD to the inflammatory lesions in the lung cysts is required. Accordingly, a gene therapy, in which the DLAD expression vector is introduced into cells at or around the inflammatory lesion, is effective as a sustainable therapeutic method for CF. For the purpose of preventing viral infection of livestock and the like, a transgenic animal having enhanced preventive function against infection, can be produced by introducing the DLAD expression vector into the embryonic cells.

The vector to be used can be selected according to the administration subject, and examples of vectors preferably administered to human include viral vectors such as retrovirus, adenovirus and adeno-associated virus. Adenovirus is particularly preferable as a DLAD gene transfer vector for the treatment of CF, because it has a very high gene transfer efficiency, can be introduced even into non-dividing cells, and is trophic for the respiratory epithelium. However, since the integration of the introduced gene into the host chromosome is extremely rare, the gene expression is transient and typically lasts for about 4 weeks. In view of the sustainability of the therapeutic effect, the use of an adeno-associated virus is also preferable, which has a relatively high gene transfer efficiency, can be introduced even into non-dividing cells and can be integrated into chromosome via inverted terminal repeats (ITRs).

Examples of pharmaceutically acceptable carriers contained in the pharmaceutical composition containing a DLAD expression vector as an active ingredient may be those for the above-mentioned pharmaceutical composition containing the DLAD protein.

The vector can be introduced by either an ex vivo method, which comprises isolating the target cells from the administration subject, culturing, transferring the vector thereto and implanting the cells back into the subject, or an in vivo method, which comprises directly transferring the vector into the body of the administration subject. When the in vivo method is used, the administration of the vector via intravenous injection or the like may raise a problem of the antigenicity of the viral vector, but the undesired effects caused by the presence of the antibody can be reduced by topically injecting the vector into the organ/tissue containing the target cells (in situ method).

When a non-viral vector is used as a vector, the DLAD expression vector can be introduced using macromolecule carriers such as liposome and polylysine-DNA-protein conjugate.

The present invention also provides a pharmaceutical composition, which comprises a host cell containing the DLAD expression vector of the invention as an active ingredient. The host cells to be used may include autogenous cells, which are isolated as target cells from the administration subject in the ex vivo method of the gene therapy using the above-mentioned DLAD expression vector, cells isolated from the syngeneic or allogeneic individuals, or established cell lines derived from these cells by subculture. In another embodiment, a transformant obtained by transforming a host cell, which is normally present in the nasal cavity, pharynx, oral cavity, intestinal tract, skin, vagina and the like of the administration target animal, with a DLAD expression vector according to a conventional method, can be delivered to the site where the host cell is normally present in the administration subject.

The dose of the pharmaceutical composition containing the DLAD expression vector or the host cell, which expresses this vector of the present invention, as an active ingredient, is preferably one capable of expressing DLAD in the body of an animal to which it is administered, the dose corresponding to an amount suitable for allowing the expression to be achieved when the DLAD protein itself is administered.

The present invention is further explained in detail by way of Examples in the following. These are mere examples, which in no way limit the scope of the present invention.

EXAMPLE 1

Cloning and Sequence Analysis of Mouse DLAD cDNA

The EST subdivision of the NCBI GenBank database was screened for EST encoding an amino acid sequence homologous to the deduced amino acid sequence of human DNase II (GenBank AF060222) using the tblastn program. As a result, a mouse EST clone (GenBank AI048641) was identified. Based on the sequence of the EST clone, the following two oligonucleotide primers (GSP2/mD and GSP1/mD) were synthesized. Furthermore, the following oligonucleotide (AP1) was synthesized as a linker primer. GSP2/mD:

```
(Sequence Listing, SEQ ID NO: 5)
5'-AATGAATATGGTGAAGCTGTGGACTGG-3'
```

(sequence identical to the nucleotide sequence of the nucleotide Nos. 300 to 326 of the nucleotide sequence shown in Sequence Listing, SEQ ID NO: 2) GSP1/mD:

```
(Sequence Listing, SEQ ID NO: 6)
5'-CCATCGTTGTATATTAGATAGGCTGTG-3'
```

(sequence complementary to the nucleotide sequence of the nucleotide Nos. 509 to 535 of the nucleotide sequence shown in Sequence Listing, SEQ ID NO: 2) AP1:

```
(Sequence Listing, SEQ ID NO: 7)
5'-CCATCCTAATACGACTCACTATAGGGC-3'
```

Using the following primers containing oligo dT: 5'-

```
(Sequence Listing, SEQ ID NO: 8)
5'-TTCTAGAATTCAGCGGCCGC(T₃₀)VN-3'
```

(wherein V is G, A or C, and N is G, A, C or T) a reverse transcription reaction was performed using C57black/6 mouse liver-derived poly A(+) RNA as a template to generate a single strand cDNA (antisense strand). The sense strand was further synthesized according to a conventional method to give a double strand DNA followed by ligation of the linker DNA containing the AP1 sequence to its both ends. Using this cDNA as a template, 3' RACE reaction was performed with GSP2/mD as a sense primer and AP1 as an antisense primer, and then 5' RACE reaction was performed with AP1 as a sense primer and GSP1/mD as an antisense primer. Marathon cDNA Amplification kit (Clontech) was used in these RACE reactions. Each amplification product was subcloned into pBLUESCRIPT KS+ phagemid vector (Stratagene), and the nucleotide sequence of each insert was determined by cycle sequencing using 7-Deaza Thermo Sequenase kit (Amasham) and DSQ1000L DNA sequencer (Shimazu).

As a result, it was revealed that the mRNA containing the EST clone sequence with homology to DNase II as a partial sequence consists of the nucleotide sequence shown in Sequence Listing, SEQ ID NO: 2. The 3' RACE reaction resulted in two cDNA fragments that differ in their polyadenylation sites. Poly A-added signal consensus sequences (AATAAA) are found at 14 nucleotides upstream of the first polyadenylation site (the nucleotide No. 1409) and 18 nucleotides upstream of the second polyadenylation site (the nucleotide No. 1634), which are consistent with this observation.

Sequence analysis revealed that this cDNA sequence contains an ORF of 1065 bp (the nucleotide Nos. 213 to 1277) encoding 354 amino acids of a novel polypeptide. The ORF had 37.1% amino acid identity with DNase II. The molecular weight of the polypeptide encoded by the ORF, which is calculated from the deduced amino acid sequence, was 40,767. On the basis of the enzymological properties (see below) of the recombinantly produced protein, the present inventors designated this novel protein as DNase II-Like Acid DNase (DLAD).

DLAD is a highly basic protein (isoelectric point: 9.67) containing 8 potential N-glycosylation sites [the Asn residue of Asn-Xaa-Thr/Ser (Xaa is an optional amino acid); the amino acid Nos. 48, 55, 76, 92, 107, 186, 249 and 297 of the amino acid sequence shown in Sequence Listing, SEQ ID NO: 1]. The possible N terminal signal peptide was predicted to be the first 22 amino acids (the amino acid Nos. -22 to -1) by von Heijne's method [*Nucleic Acids Res.*, 14: 4683-4690 (1986)].

A homology search of the GenBank database revealed that DLAD has 32.1%, 25.1% and 19.4% amino acid identities with three proteins, C07B5.5, F09G8.2 and K04H4.6, encoded by putative ORFs of a nematode *C. elegans* genome, respectively. Furthermore, DLAD shares 37.5% amino acid identity with FP-CELL encoded by the third ORF of FWPV genome, which value is higher than the identity between DNase II and FP-CELL (28.4%).

EXAMPLE 2

Tissue Distribution of DLAD mRNA

Northern blot analysis was performed to assess the expression of DLAD mRNA in various mouse tissues. Total RNA was extracted from each tissue (brain, thymus, lung, heart, liver, stomach, small intestine, spleen, kidney and testis) of adult mouse with TRIzol reagent (Gibco BRL). Each RNA aliquot (15 μg) was subjected to 1% agarose-formamide gel electrophoresis and blotted onto a Biodyne-A membrane (Paul). This membrane was subjected to the hybridization with a $^{32}$P-labeled probe, obtained by random priming of Xho I digestion fragment of pcDLAD-Myc-His (see below), which is a vector carrying the DNA encoding a DLAD-Myc fusion protein with a histidine tag, in hybridization solution consisting of 5×SSPE, 5× Denhardt's solution, 50% formamide, 0.1% SDS and 100 μg/ml heat-denatured salmon sperm DNA at 42° C. overnight. The hybridization solution was removed after the reaction, and the membrane was washed with 0.1×SSC, 0.1% SDS at 50° C. and exposed to X-ray film at -80° C. for 5 days using an intensifying screen. As a result, a single band corresponding to the 1.9 kb DLAD mRNA was detected only in the liver. This liver-specific expression is contrastive with the poor organ-specificity of DNase II, clearly suggesting the distinct physiological function of DLAD from that of DNase II.

EXAMPLE 3

Localization of DLAD Protein

The primary structure analysis of DLAD in Example 1 revealed that the primary translation product of DLAD has a hydrophobic domain satisfying the requirement for a signal peptide at the N terminus. That is, it was suggested that DLAD was a secretory protein. Then, to confirm this, a DLAD expression vector was introduced into a human cultured cell followed by comparison of the presence ratio of intracellular/extracellular DLADS. The subcellular localization of DLAD present within the cell was also analyzed.

(1) Construction of DLAD Expression Vector

RT-PCR reaction was performed with C57black/6 mouse liver-derived poly A(+) RNA as a template, using the following pair of primers to generate a cDNA fragment containing DLAD ORF without termination codon, and the resulting cDNA fragment was subcloned into pBLUESCRIPT KS+.

Senseprimer:

(Sequence Listing, SEQ ID NO: 9)
5'-CTCGAGCCACCATGACAGCAAAGCCTCTAAGAACA-3'

(sequence with a linker sequence containing Xho I recognition site (CTCGAG) added to the 5' terminus of the nucleotide sequence of the nucleotide Nos. 213 to 236 of the nucleotide sequence shown in Sequence Listing, SEQ ID NO: 2)

Antisense Primer:

(Sequence Listing, SEQ ID NO: 10)
5'-CTCGAGACTTACAGAACCCATAACGGAGAT-3'

(sequence with a linker sequence containing Xho I recognition site (CTCGAG) added to the 5' terminus of the sequence complementary to the nucleotide sequence of the nucleotide Nos. 1252 to 1274 of the nucleotide sequence shown in Sequence Listing, SEQ ID NO: 2)

After confirming the sequence by cycle sequencing, the insert DNA was excised by Xho I digestion and re-cloned into the Xho I sites of pcDNA3-Myc-His C (Invitrogen) and pEGFP-N3 (Clontech) to generate expression vectors encoding DLAD with C terminal Myc and histidine tags (pcDLAD-Myc-His) and encoding DLAD-GFP (Green Fluorescence Protein) fusion protein (pDLAD-GFP), respectively. For comparison, an expression vector encoding DNase II with C terminal Myc and histidine tags (pcDNaseII-Myc-His) was generated by the same procedure.

Furthermore, to assess the secretion efficiency of DLAD signal peptide, an expression vector encoding a chimeric protein, in which the signal peptide of DLAD is replaced with that of DNase II (pcDNaseII/DLAD), was produced in the following procedure. DNA fragments encoding the DNase II signal peptide and encoding DLAD without signal peptide were amplified by PCR respectively using the following two pairs of primers. The resulting fragments were ligated after Hae II digestion and subcloned into pBLUESCRIPT KS+. phagemid After confirming the sequence, the insert was re-cloned into pcDNA3-Myc-His C to give pcDNaseII/DLAD.

Amplification of DNase II Signal Peptide Coding Sequence
Sense Primer:

(Sequence Listing, SEQ ID NO: 11)
5'-CTCGAGCCACCATGATCCCGCTGCTGCTGGCA-3'

Antisense Primer:

(Sequence Listing, SEQ ID NO: 12)
5'-GCAGGTCAGGGCGCCGGC-3'

Amplification of Signal Peptide(−) DLAD Coding Sequence
Sense Primer:

(Sequence Listing, SEQ ID NO: 13)
5'-AGCTAGGCGCCCTCTCATGCAGAAATGAA-3'

Antisense Primer:

(Sequence Listing, SEQ ID NO: 10)
5'-CTCGAGACTTACAGAACCCATAACGGAGAT-3'

(2) Transfection and Western Blot Analysis

HeLa S3 cells ($2 \times 10^5$) grown in RPMI 1640 medium supplemented with 10% fetal calf serum were transfected individually with 1 µg of pcDLAD-Myc-His, pcDNaseII/DLAD or pcDNaseII-Myc-His using FuGene6 transfection reagent (Boehringer). After incubating for 48 hr, the culture supernatant (extracellular fraction) and the cell were collected separately. The cells were homogenized in 2 ml of ice-cold buffer A [100 mM Tris-HCl (pH7.8), 3 mM $MgCl_2$, 1 mM 2-mercaptoethanol and 0.3 mM PMSF] containing 0.1% Nonidet P-40 with a Teflon-glass homogenizer by 10 strokes. The homogenate was centrifuged at 10,000×g for 10 min and the supernatant was recovered as intracellular (cytoplasmic) fraction. Recombinant proteins with histidine-tags were purified from the intracellular and extracellular fractions, respectively, using Ni-NTA spin column (Quiagen) according to the manufacture's protocol. After concentration with Ultrafree MC (Millipore), aliquots of the eluates were subjected to 10% SDS-PAGE and transferred onto Immobilon P membrane (Millipore). The membrane was blocked in TBST [20 mM Tris-HCl (pH8.0), 400 mM NaCl and 0.05% (w/v) Triton X-100] containing 2.5% bovine serum albumin for 1 hr and reacted with mouse anti-Myc antibody (Novagen). After washing with TBST, the antibody retained on the membrane was detected using anti-mouse IgG (Promega) labeled with an alkaline phosphatase. The staining image was scanned with a CCD camera (Atto) and the optical densities of the bands were quantified by densitometry (NIH image 1.60). The results are shown in FIG. 1.

The DLAD with Myc and His-tags was detected as a single band of 58 kDa. Calculating the molecular weight (about 3 kDa) of the Myc and His-tags added to C terminus, the molecular weight of DLAD per se is estimated as about 55 kDa by SDS-PAGE, which value is larger than the molecular weight 38,452 Da deduced from the amino acid sequence (the amino acid Nos. 1 to 332) of DLAD. This appears to be due to glycosylation.

While about 80% of DNase II was secreted extracellularly, about 70% of DLAD retained within the cells and about 30% was found in the extracellular fraction (FIG. 1). Since DLAD is as stable as DNase II in the medium for HeLa S3 cells, the low presence ratio of extracellular DLAD is not due to the rapid degradation of DLAD in the medium. The inefficient secretion of DLAD was not improved by replacing its signal peptide with that of DNase II, which indicates that this inefficiency is not due to weak secretion signal of DLAD itself. Thus, it is suggested that some targeting motif(s) as intracellular retention signal(s) exist in the mature DLAD protein.

(3) Fluorescence Microscopic Analysis of DLAD-GFP Fusion Protein

HeLa S3 cells ($2 \times 10^5$) grown on a coverslip were transfected with pDLAD-GFP (1 µg) in the same manner as in (2) above. The cells were incubated for 48 hr and fixed with 1% glutaraldehyde in PBS(−) at room temperature for 10 min. After washing the coverslip with PBS(−), the cell nuclei were stained with 1 mM Hoechst 33258 in PBS(−) and the images of GFP and DNA were observed by a fluorescence microscope (Olympus). As a control, HeLa S3 cells engineered to express GFP alone was observed in the same manner. As a result, while GFP gave a diffuse image expanded both in the cytoplasmic and nuclear regions in cytoplasm, DLAD-GFP fusion protein was detected as a granular pattern. These suggest that the intracellular DLAD is localized in cytoplasm and targeted some organelle. A motif search using PSORT II program revealed that DLAD contains no transition signals for mitochondria or nuclei. Thus, it is speculated that a possible target organelle for the cytoplasmic DLAD is acidic organelle such as lysosome or peroxysome.

EXAMPLE 4

Analysis of the Enzymological Properties of DLAD (1) Purification of Recombinant DLAD In the same manner as in (2) of Example 3, HeLa S3 cells ($5\times10^6$) were transfected with 25 µg of pcmDLAD-Myc-His or pcmDNaseII-Myc-His, individually. These plasmids encode the mature proteins of DLAD and DNase II, respectively, wherein Myc and His-tags are added to their C termini. After incubation of the cells for 48 hr, recombinant DLAD and recombinant DNase II were purified by IMAC using Ni-NTA spin column, in the same manner as in (2) of Example 3. The purified DLAD (or DNase II), which was eluted in 300 µl of elution buffer [50 mM sodium phosphate (pH 8.0) containing 250 mM imidazole and 300 mM NaCl], was dialyzed against 20 mM Mes-NaOH containing 1 mM 2-mercaptoethanol and used in the following assay for enzyme activities. The Sample obtained by treating HeLa S3 cells transfected with empty vector in the same manner was used as a control.

In the following experiments, the assay for DNase activity was performed as below, unless otherwise described. 20 µl of reaction mixture [50 mM Mes-NaOH (pH 5.2), 1 mM 2-mercaptoethanol, 1 unit of enzyme, 500 ng supercoiled or EcoR I-digested linear pBLUESCRIPT KS+ phagemid vector] was prepared on ice and incubated at 45° C. for 20 min. The reaction was terminated with phenol/chloroform and 5 µl aliquot of the reaction mixture was subjected to 1% agarose gel electrophoresis. After ethidium bromide staining, the image was scanned with CCD camera (Atto) under UV transillumination and optical density of the band corresponding to the full length substrate DNA was quantified by densitometry (NIH image 1.60). DNase activity was determined using reduction of the band intensity corresponding to the full length substrate DNA as an index. In the present invention, 1 unit of DLAD and DNase II activities are defined as their amounts required to decrease the band intensity corresponding to 200 ng of the full length substrate DNA under the above-mentioned reaction conditions.

(2) Divalent Cation-dependency

Using a supercoiled plasmid as a substrate, DLAD activities in the presence and absence of a divalent cation chelator were determined under acidic (50 mM Mes-NaOH, pH 5.2) and neutral (50 mM Mops-NaOH, pH 7.2) conditions, respectively. 1 mM of EDTA and EGTA were used individually, as chelators. As a result, DLAD exhibited an endonuclease activity catalyzing the degradation of the supercoiled plasmid DNA under both pH conditions. However, DLAD activity under acidic condition was much higher than that under neutral condition. The addition of divalent cation chelator, EDTA or EGTA had no effect on DLAD activity regardless of pH ranges. Thus, DLAD was demonstrated to be a divalent cation-independent acid DNase. No endonuclease activity was detected in the same assays using the sample derived from HeLa S3 cells transfected with empty vector, indicating that the DLAD activity detected is not due to contamination of the endogenous DNases in HeLa S3 cells.

(3) Active pH Range and Optimal pH

Using a supercoiled plasmid as a substrate, DLAD and DNase II activities were determined under the above-mentioned standard conditions except varying kinds of buffers and pH [i.e., acetate-NaOH (pH 4.0 and 4.4), Mes-NaOH (pH 4.8, 5.2, 5.6, 6.0 and 6.4) and Mops-NaOH (pH 6.4, 6.8, 7.2 and 7.6)]. As a result, DLAD showed its DNase activity in all of the pH ranges examined with a maximum at pH 5.2 in Mes-NaOH. However, DNase II activity was observed only at pH 5.6 or below.

(4) Sensitivity Against Inhibitors

Figure 2:
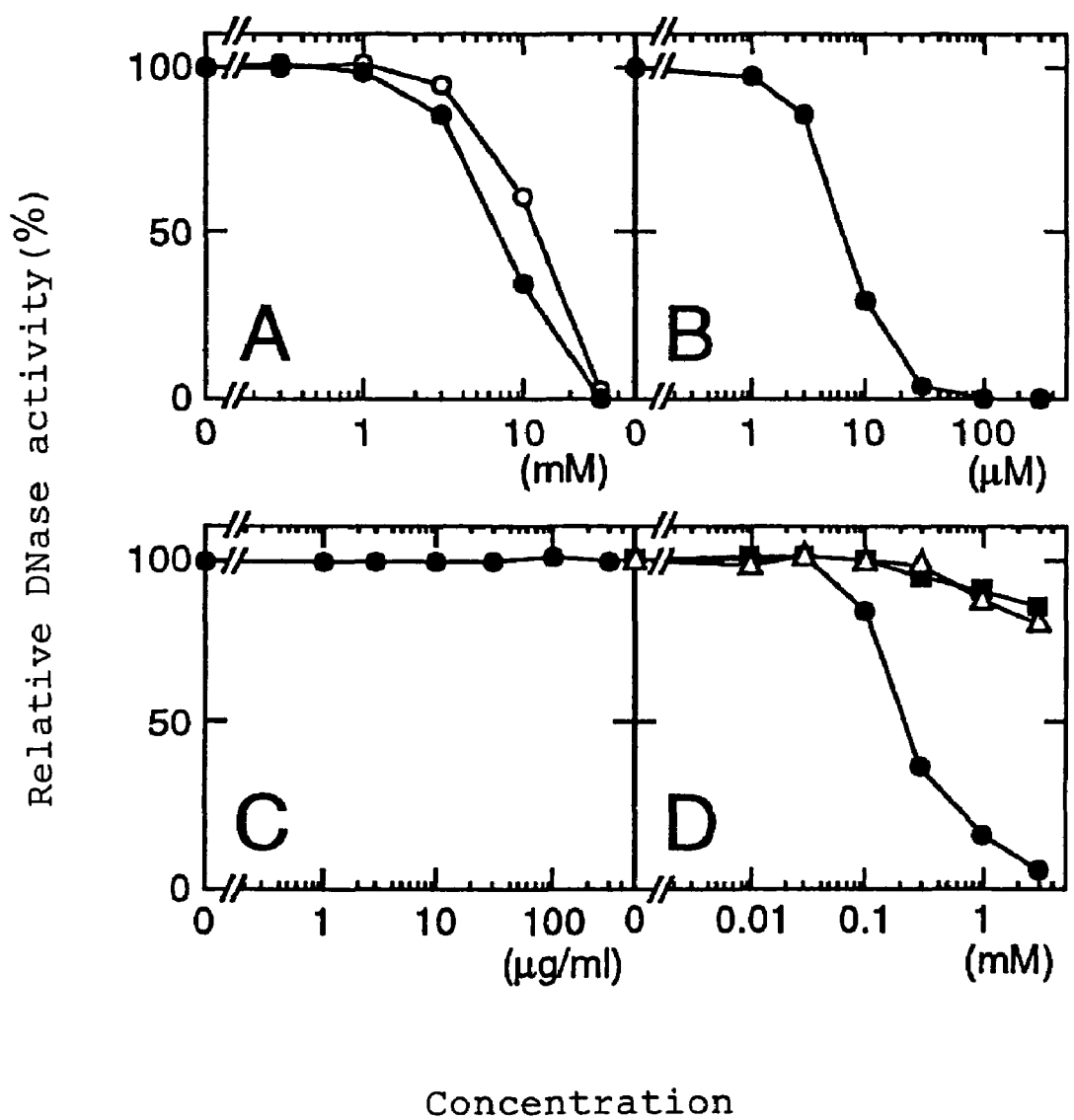
FIG. 2 shows sensitivity of DLAD to various DNase inhibitors, wherein A (○): $MgCl_2$, (●): $MgSO_4$; B: aurintricarboxylic acid; C: G-actin; D (■): $CoCl_2$, (△): $NiCl_2$, (●): $ZnCl_2$.

DLAD activities were determined in the presence of various concentrations of DNase inhibitors [$MgCl_2$ (FIG. 2A, ○), $MgSO_4$ (FIG. 2A, ●), aurintricarboxylic acid (FIG. 2B), G-actin (FIG. 2C), $CoCl_2$ (FIG. 2D, ■), $NiCl_2$ (FIG. 2D, △) and $ZnCl_2$ (FIG. 2D, ●)] under the above-mentioned standard conditions to analyze its sensitivity against the inhibitors. As a result, high concentrations of $MgCl_2$ inhibited DLAD activity ($IC_{50}$=13 mM). $MgSO_4$, an inhibitor of DNase II, inhibited DLAD more efficiently than $MgCl_2$ ($IC_{50}$=7 mM), indicating that $SO_4^{2-}$ ion is effective to inhibit DLAD. Aurintricarboxylic acid, a general inhibitor of nucleases, strongly inhibited DLAD ($IC_{50}$=6 µM), whereas G-actin, an inhibitor of DNase I, did not inhibit DLAD. The comparison of the sensitivity to three divalent metal ions revealed that DLAD is most sensitive to $Zn^{2+}$ ($IC_{50}$=0.2 mM). In contrast, it is known that there are little differences between these three divalent metal ions in inhibitory effect on DNase II [*J. Biochem.*, 87: 1097-1103 (1980)].

(5) Mode of DNA Hydrolysis

Using a supercoiled pBLUESCRIPT KS+ phagemid vector as a substrate, enzyme reaction of DLAD or DNase II was performed under the above-mentioned standard conditions. After terminating the reaction, contaminants were removed by phenol/chloroform treatment to isolate degraded plasmid DNA. The 3' ends were labeled in 50 µl of a reaction solution consisting of 20 units of terminal deoxynucleotidyl transferase (Toyobo), 0.83 mCi/ml [$\gamma$-$^{32}$P]dCTP, 100 mM sodium cacodylate (pH 7.2), 0.2 mM DTT and 1 mM $CoCl_2$. The 5' ends were labeled in 50 µl of a reaction solution consisting of 20 units of polynucleotide kinase (Toyobo), 0.83 mCi/ml [$\gamma$-$^{32}$P]ATP, 50 mM Tris-HCl (pH 8.0), 10 mM $MgCl_2$ and 10 mM 2-mercaptoethanol. The end-labeling treatments were performed as to both DNAs with and without pretreatment with 20 units of calf intestinal alkaline phosphatase (Takara) in the presence of 50 mM Tris-HCl (pH 8.0) and 1 mM $MgCl_2$ to remove the phosphoryl groups in the ends of DNAs, respectively. Unincorporated nucleotides were removed by ethanol precipitation. The labeled DNA was subjected to 1% agarose gel electrophoresis, transferred onto nylon membrane and analyzed with BAS 1500 image analyzer (Fuji Film). As a result, in both DNA fragments treated with DLAD and DNase II, the 5' ends were labeled regardless of pretreatment with alkaline phosphatase, whereas the 3' ends could be labeled only after removal of the phosphoryl groups. Thus, it is revealed that DLAD catalyzes DNA hydrolysis to generate 3'-P/5'-OH ends as DNaseII does.

EXAMPLE 5

Suppression Effects of DLAD on the Expression of Foreign DNA (1) Isolation of Rat DLAD cDNA Using the same strategy as in Example 1, a rat EST clone (GenBank AF178974) encoding the amino acid sequence with homology to the deduced amino acid sequence of human DNase II was identified. Oligonucleotide primers were synthesized based on the nucleotide sequence of this clone, followed by the RACE with liver poly A(+) RNA derived from Wister rat, which is connately pigment-deficient (albino), as a template to clone the full length rat DLAD cDNA. From the sequence analysis by a conventional method, it was deduced that this cDNA contains an ORF encoding 356 amino acids with a signal peptide consisting of 22 amino acids at the N terminus. It was found to have 83.3% DNA identity and 70.8% amino acid identity to mouse DLAD. An expression vector encoding rat DLAD with Myc and His-tags at the C terminus (prDLAD-Myc-His) was constructed by the same strategy as in (1) of Example 3. HeLa S3 cells were transfected with this vector to generate a recombinant rat DLAD. Characterization of the obtained recombinant protein confirmed that this protein has properties similar to mouse DLAD in active pH range, divalent cation-dependency, mode of DNA cleavage, sensitivity to inhibitors and the like.

Figure 3:
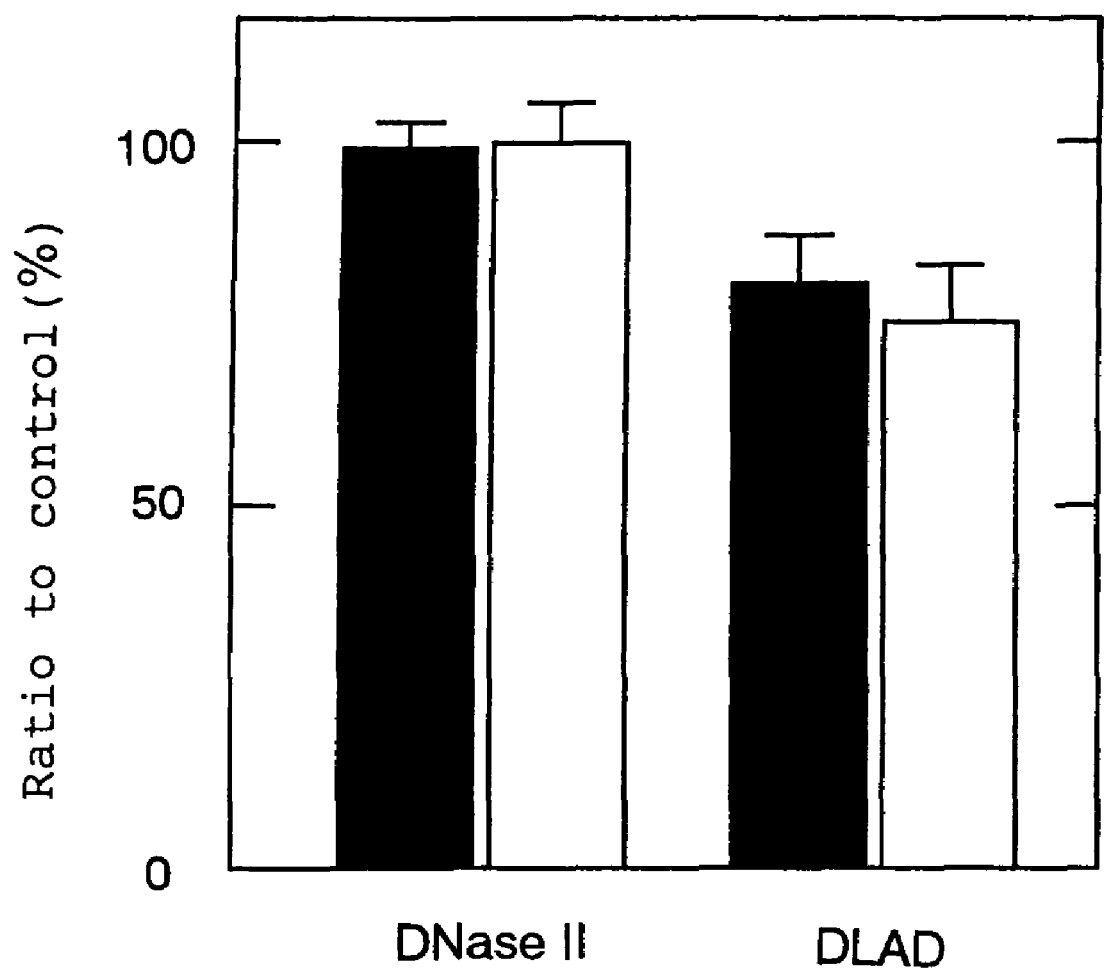
FIG. 3 shows GFP or β-galactosidase activity in HeLa S3 cells co-transfected with a DLAD or DNase II expression vector and a GFP (closed column) or β-galactosidase (open column) expression vector. The activities are shown as the ratio (%) to the activity in the HeLa S3 cells co-transfected with a control vector and a reportor gene expression vector. The data are the average values (column) of 3 independent experiments±standard error (error bar).

(2) Suppression of the Expression of Foreign Reporter Gene in DLAD Expressing HeLa Cells HeLa S3 cells ($2 \times 10^5$) grown on a coverslip were co-transfected with prDLAD-Myc-His (1 µg) and pcDNA3.1-Myc-His/lac Z (β-galactosidase expression vector; Invitrogen) or pEGFP-N3 (Clontech; supra) (0.5 µg), using the same method as in (2) of Example 3. Assay for GFP activity was performed according to the method described in (3) of Example 3. β-galactosidase activity was determined with β-galactosidase assay system (Promega) according to the attached protocol. The same experiments were performed using an expression vector encoding rat DNase II in place of DLAD with Myc and His-tags at the C terminus (prDNaseII-myc-His). An empty vector, pcDNA3.1-Myc-His (Invitrogen), was used as a control. The results are shown in FIG. 3.

As seen from the figure, while DNase II has no effect on the expression of the foreign reporter genes, DLAD suppressed the expression of these foreign genes by about 20 to 25% versus control. These observations suggest that DLAD has an effect to act on heterologous DNA entering into cells such as viral DNA, and degrade and remove the DNA.

EXAMPLE 6

Isolation of Human DLAD cDNA

Using the same strategy as in Example 1, a human EST clone (GenBank No. AA988125) encoding the amino acid sequence with homology to the amino acid sequence of mouse DLAD was identified. On the basis of the nucleotide sequence of this clone, the following primers: GSP2/h2L:

(Sequence Listing, SEQ ID NO: 14)
5'-AACTGCTCCCTTCCTTACCATGTCTAC-3'

(sequence identical to the nucleotide sequence of the nucleotide Nos. 832 to 858 of the nucleotide sequence shown in Sequence Listing, SEQ ID NO: 4) GSP1/h2L:

(Sequence Listing, SEQ ID NO: 15)
5'-GAAGGCTTGGTGTGGACTCCGATTTAG-3'

(sequence complementary to the nucleotide sequence of the nucleotide Nos. 973 to 999 of the nucleotide sequence shown in Sequence Listing, SEQ ID NO: 4) were synthesized and, further using the above-mentioned linker primer AP1 together with these primers, RACE was performed with human liver-derived poly A(+) RNA as a template to clone the full length human DLAD cDNA. From the sequence analysis by a conventional method, it was deduced that this cDNA contains an ORF (Sequence Listing, SEQ ID NO: 4) encoding 361 amino acids (Sequence Listing, SEQ ID NO: 3) with a signal peptide consisting of 27 amino acids at the N terminus. It was found to have 75.1% DNA identity and 65.4% amino acid identity to mouse DLAD. An expression vector encoding human DLAD with Myc and His-tags at the C terminus (phDLAD-Myc-His) was constructed by the same strategy as in (1) of Example 3. HeLa S3 cells were transfected with this vector to generate a recombinant human DLAD. Characterization of the obtained recombinant protein confirmed that this protein has properties similar to mouse DLAD in active pH range, divalent cation-dependency, mode of DNA cleavage, sensitivity to inhibitors and the like.

Free Text in Sequence Listing

SEQ ID NO: 5: Oligonucleotide designed to act as sense primer for amplifying 3'-terminal of mouse DLAD cDNA.

SEQ ID NO: 6: Oligonucleotide designed to act as antisense primer for amplifying 5'-terminal of mouse DLAD cDNA.

SEQ ID NO: 7: Oligonucleotide designed to act as linker primer for amplifying 5'- and 3'-terminals of DLAD cDNA.

SEQ ID NO: 8: Oligonucleotide designed to act as primer for reverse transcription of mouse DLAD RNA, wherein v is g, a or c and n is g, a, c or t.

SEQ ID NO: 9: Oligonucleotide designed to act as sense primer for amplifying full length mouse DLAD cDNA.

SEQ ID NO: 10: Oligonucleotide designed to act as antisense primer for amplifying full length mouse DLAD cDNA.

SEQ ID NO: 11: Oligonucleotide designed to act as sense primer for amplifying coding sequence of DNase II signal peptide.

SEQ ID NO: 12: Oligonucleotide designed to act as antisense primer for amplifying coding sequence of DNase II signal peptide.

SEQ ID NO: 13: Oligonucleotide designed to act as sense primer for amplifying coding sequence of DLAD lacking its signal peptide.

SEQ ID NO: 14: Oligonucleotide designed to act as sense primer for amplifying 3'-terminal of human DLAD cDNA.

SEQ ID NO: 15: Oligonucleotide designed to act as antisense primer for amplifying 5'-terminal of human DLAD cDNA.

This application is based on application No. 11-230870 filed in Japan, the contents of which are incorporated hereinto by reference.

All of the references cited herein containing patents and patent applications are herein incorporated by reference to the same extent as if each individual publication was specifically described herein.

The invention claimed is:

1. A composition comprising:
   (a) a polypeptide comprising the amino acid sequence of amino acid Nos. 1 to 334 of SEQ ID NO: 3, and
   (b) a carrier.

2. An isolated polypeptide comprising the amino acid sequence of amino acid Nos. 1 to 334 of SEQ ID NO: 3.

3. A method for improving respiratory function of a patient suffering from cystic fibrosis, which comprises administering to the patient an effective amount of a polypeptide comprising the amino acid sequence of amino acid Nos. 1 to 334 of SEQ ID NO: 3, thereby hydrolyzing DNA in sputum of the patient to improve the respiratory function of the patient.

* * * * *